United States Patent
Kluender et al.

(10) Patent No.: US 6,288,063 B1
(45) Date of Patent: *Sep. 11, 2001

(54) SUBSTITUTED 4-BIARYLBUTYRIC AND 5-BIARYLPENTANOIC ACID DERIVATIVES AS MATRIX METALLOPROTEASE INHIBITORS

(75) Inventors: Harold Clinton Eugene Kluender, Trumbull; David Ross Brittelli, Branford; William Riley Schoen, Madison; Sookhee Nicole Ha, Woodbridge, all of CT (US)

(73) Assignee: Bayer Corporation, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/085,909

(22) Filed: May 27, 1998

(51) Int. Cl.$^7$ ..................... C07D 209/48; C07D 295/18; A61K 31/12; A61K 31/16
(52) U.S. Cl. .................. 514/243; 548/477; 548/451; 548/183; 548/319.5; 548/317.5; 548/550; 548/547; 548/263.4; 548/226; 548/510; 548/573; 548/210; 548/221; 548/309.7; 548/361.5; 548/207; 548/479; 562/621; 568/42; 568/325
(58) Field of Search ............................ 562/621; 514/575, 514/243, 373, 417; 568/42, 325; 564/99; 544/183; 548/207, 479

(56) References Cited

U.S. PATENT DOCUMENTS

| | | | |
|---|---|---|---|
| 3,322,631 | 5/1967 | Sprague et al. | 167/65 |
| 4,325,964 | * 4/1982 | Lafon | 424/282 |
| 4,738,986 | * 4/1988 | Kneen et al. | 514/575 |
| 5,665,777 | * 9/1997 | Fesik et al. | 514/575 |

FOREIGN PATENT DOCUMENTS

| | | | |
|---|---|---|---|
| 0252639 | 1/1988 | (EP) | C07C/149/40 |
| 9615096 | 5/1996 | (WO) | C07C/59/88 |
| 9723459 | 3/1997 | (WO) | C07D/211/34 |
| 9718188 | 5/1997 | (WO) | A61K/31/19 |
| 9724117 | 7/1997 | (WO) | C07C/259/06 |
| 9743237 | 11/1997 | (WO) | C07C/59/84 |
| 9743238 | 11/1997 | (WO) | C07C/59/90 |
| 9743239 | 11/1997 | (WO) | C07C/59/90 |
| 9743240 | 11/1997 | (WO) | C07C/59/90 |
| 9743245 | 11/1997 | (WO) | C07C/229/34 |
| 9743247 | 11/1997 | (WO) | C07C/235/84 |

OTHER PUBLICATIONS

Chemical Abstract 116:166243, 1992.
Chemical Abstract 101:191365, 1984.
Chemical Abstract 122:133115, 1995.
Chemical Abstract 108:94047, 1988.
Chemical Abstract 99:5478, 1983.
Chemical Abstract 124:220549, 1996.
Chemical Abstract 105:172404, 1986.
Trost, et al., A Ru–Catalyzed Three–Component Addition to Form 1,5–Diketones, J. Am. Chem. Soc., 119, 836–837 (1997).
Padwa, et al., Ligand–Induced Selectivity in the Rhodium (II)–Catalyzed Reactions of α–Diazo Carbonyl Compounds, J. Org. Chem., 61, 63–72 (1996).

(List continued on next page.)

*Primary Examiner*—Mukund J. Shah
*Assistant Examiner*—Deepak R. Rao

(57) ABSTRACT

Inhibitors for matrix metalloproteases, pharmaceutical compositions containing them, and a process for using them to treat a variety of physiological conditions. The compounds of the invention have the generalized formula

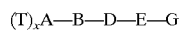

wherein A is an aryl or heteroaryl rings; B is an aryl or heteroaryl ring or a bond; each T is a substituent group; x is 0, 1, or 2; the group D represents

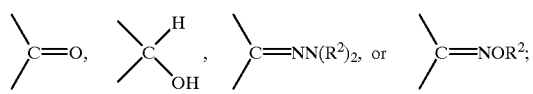

the group E represents a two or three carbon chain bearing one to three substituent groups which are independent or are involved in ring formation, possible structures being shown in the text and claims; and the group G represents

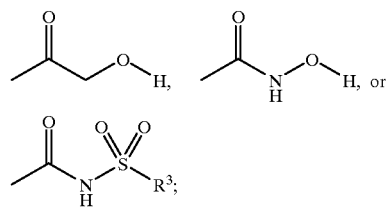

and with the proviso that when G is

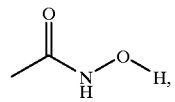

each of the substituents on E is an independent substituent; and include pharmaceutically acceptable salts thereof.

13 Claims, No Drawings

OTHER PUBLICATIONS

Morandini, et al., The proximal pathway of metabolism of the chlorinated signal molecule differentiation–inducing factor 1 (DIF–1) in the cellular slime mould Dictyostelium, Biochem. J., 306, 735–743 (1995).

Fairfax, et al., Alternatives to α–Diazo Ketones for Tandem Cyclization–Cycloaddition an Carbenoid–Alkyne Metathesis Strategies. Novel Cyclic Enol–Ether Formation via Carbonyl Ylide Rearrangement Reactions, J. Chem. Soc., Perkin Trans., 1, 2837–2844 (1992).

Seed, Chemical Abstract 126:139316, 1997.*

Kohler, E.P, "Isoxazoline Oxides. VIII", Journal of the American Chemical Society, 50(1):221–228(Jan. 1928).

Tamam, G.H., Hamed, A.A., El–Mobyed, M., and Mohamed, A.Y., "Alkylation Reaction and Michael Condensation of 3–Aroyl Acrylic Acids", Egyptian Journal of Chemistry, 2B(4):331–339 (1985).

Chem. abstr., vol. 122, No. 11, Mar. 13, 1995 (Columbus, OH, USA), p. 1111, column 2, the abstract No. 133115a, ARIEF, M.M. "Studies on alpha–[6–(2'methoxynaphthalenyl)–4–phenylpyrimidinylthio]–β–(4–phenylbenzoyl)propionic acid and the biological activity of some products".

* cited by examiner

SUBSTITUTED 4-BIARYLBUTYRIC AND 5-BIARYLPENTANOIC ACID DERIVATIVES AS MATRIX METALLOPROTEASE INHIBITORS

FIELD

This invention relates to enzyme inhibitors, and more particularly, to novel matrix metalloprotease-inhibiting 4-Biarylbutyrohydroxamic Acids, 5-Biarylpentanohydroxamic Acids, 5-Biaryl-1-hydroxy-2-pentanones, 6-Biaryl-1-hydroxy-2-hexanones, N-(4-Biarylbutyryl)sulfonamides and N-(5-Biarylpentanoyl)sulfonamides and derivatives thereof.

BACKGROUND

The matrix metalloproteases (aka. matrix metalloendoproteinases or MMPs) are a family of zinc endoproteinases which include, but are not limited to, interstitial collagenase (aka. MMP-1), stromelysin (aka. proteoglycanase, transin, or MMP-3), gelatinase A (aka. 72 kDa-gelatinase or MMP-2) and gelatinase B (aka. 95 kDa-gelatinase or MMP-9). These MMPs are secreted by a variety of cells including fibroblasts and chondrocytes, along with natural proteinatious inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (A. Ho, H. Nagase, Arch Biochem Biophys., 267, 211–16 (1988); Y. Ogata, J. J. Enghild, H. Nagase, J. Biol. Chem., 267, 3581–84 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (P. G. Winyard, Z. Zhang, K. Chidwick, D. R. Blake, R. W. Carrell G., Murphy, FEBS Letts., 279, 1, 91–94 (1991)). Inhibitors of MMP-3 could thus influence the activity of other destructive proteinases by modifying the level of their endogenous inhibitors.

MMP inhibitors may also be useful in the inhibition of other mammalian metalloproteases such as the adamalysin family (or ADAMs) whose members include TNFα converting enzyme (TACE) and ADAM-10, which can cause the release of TNF from cells.

A number of diseases or conditions are thought to be mediated by excess or undesired matrix-destroying metalloprotease activity or by an imbalance in the ratio of the MMPs to the TIMPs or through the action of the release of TNF. These include: a) osteoarthritis (Woessner, et al., *J. Biochelogical Chem* 1984., 259(6), 3633–3638; *J. Rheumatol.* 1983, 10, 852–860; M. Zafarullah, et al., *J. Rheumatol.* 1993, 20, 693–697; H. J. Andrews, et al., *Agents Actions* 1992, 37, 147–154; A. J. Ellis, et al., *Biochem. Biophys. Res. Commun.* 1994, 201, 94–101), b) rheumatic diseases and conditions such as autoimmune disease, rheumatoid arthritis (D. E. Mullins, et al., *Biochim. Biophys. Acta* 1983, 695, 117–214; *Arthritis and Rheumatism* 1977, 20, 1231–1239; *Arthritis and Rheumatism* 1991, 34, 1076–1105; Maini. *J. Royal Coll. Physicians London* 1996, 30, 344), c) septic arthritis (R. J. Williams, et al., *Arthr. Rheum.* 1990, 33, 533–41), d) cancer including tumor growth, tumor metastasis and angiogenesis (R. Reich, et al., *Cancer Res.* 1988, 48, 3307–3312; MucWierzgon et al. *J. Biol. Regulators Homeostatic Agents* 1996, 10, 25; Levy et al. *Crit. Rev. Immunol.* 1996,16, 31; G. Taraboletti, et al., *J. Nat. Cancer Institute* 1995, 87, 293; R. Benelli, et al., *Oncology Research* 1994, 6, 251–257; and L M. Matrisian, et al., *Proc. Nat'l. Acad. Sci.* 1986, USA, 83, 9413–7; Y. A. DeClerck, et al., *Cancer Res.* 1992, 52, 701–708; A. Y. Strongin, et al., *J. Biol. Chem.* 1993, 268, 14033–14039; A. Melchiori, et al., *Cancer Res.* 1992, 52, 2353–2356; Davies, et al., *Cancer Res.* 1993, 53, 2087–2091; W. L. Monsky, et al., *Cancer Res.* 1993, 53, 3159–3164), e) periodontal diseases (C. M. Overall, et al., *J. Periodontal Res.* 1987, 22, 81–88), f) corneal ulceration (F. R. Burns, et al., *Invest. Opthalmol.* 1989, 30, 1569–1575), g) proteinuria (W. H. Baricos, et al., *Biochem. J.* 1988, 254, 609–612), h) various cardiovascular and pulmonary diseases such as atherosclerosis (A. M. Henney, et al., *Proc. Nat'l. Acad. Sci. USA* 1991, 88, 8154–8158), thrombotic events (Sawicki, et al. *Nature* 1997, 386, 616–619), atheroma, hemodynamic shock, unstable angina, restenosis, heart failure, i) aneurysmal diseases including those of the aorta, heart or brain (N. Vine and J. T. Powell, *Clin. Sci.* 1991, 81, 233–9), j) birth control (J. F. Woessner, et al., *Steroids* 1989, 54, 491–499), k) dystrophobic epidermolysis bullosa (A. Kronberger, et al., *J. Invest. Dermatol.* 1982, 79, 208–211), l) degenerative cartilage loss following traumatic joint injury (L. A. Walakovits, et al., *Arthritis Rheum.* 1992, 35, 35–42), m) osteopenias and other diseases of abnormal bone loss including osteoporosis (Pacifici et al. *J. Bone Mineral Res.* 1996, 11, 1043), n) tempero mandibular joint disease, o) pulmonary diseases such as chronic obstructive pulmonary disease, p) demyelinating diseases of the nervous system such as multiple sclerosis (M. S.; Coyle. *Adv. Neuroimmunol.* 1996, 6, 143; Matusevicius et al. *J. Neuroimmunol.* 1996, 66, 115); Brosnan et al. *Brain Pathol.* 1996, 6,243 and *J. Neurochem.* 1988, 50, 688–694; R. Martin and H. F. McFarland, *Crit. Rev. Clin. Lab. Sci.* 1995, 32, 121–182), q) metabolic diseases including diabetes and obesity mediated by insulin resistance (Stephens et al. *J. Biol. Chem.* 1997, 272, 971; Ofei et al. *Diabetes* 1996, 45, 881), macular degeneration and diabetic retinopathy mediated by agiogenesis, cachexia, premature skin aging (G. J. Fisher, et al., *New Eng. J. Med.* 1997, 337, 1419–1428), r) impaired wound healing including burns, s) decubital ulcers, t) acute and chronic neurodegenerative disorders (E. G. McGeer and P. L. McGeer, in D. B. Calne, ed. *Neuodegenerative Diseases*, W. B. Saunders 1994, 277–300; N. J. Rothwell and J. K. Relton, *Neurosci. Biobehav. Rerv.* 1993, 17, 217–227; W. Y. Voon, et al., *Trends Neurosci.* 1998, 21 (2), 75–80) including stroke (R. K. Clark, et al., *Brain Res. Bull.* 1993, 31, 565–572; D. Goulian and K. Vaca, *Stroke* 1993, 24 (Suppl 12), 184–190), spinal cord and traumatic brain injury (R. Martin, et al., *Annul Rev. Immunol.* 1992, 10, 153–187), amyotrophic lateral sclerosis, cerebral amyloid angiopathy (T. I. Mandybur and G. Balko, *Clin. Neuopharm.* 1992, 15, 241–247), CNS injuries in AIDS (H. E. Gendelman and M. Tardieu, *J. Leukocyte Biol.* 1994, 56, 387–388), Parkinson's disease, Alzheimer's disease (P. H. Patterson, *Cur. Opinion Neurobiol.* 1995, 5, 642–646; P. L. McGeer, et al., *Alzheimers Dis. Assoc. Disorders* 1994, 8, 149–158; J. Rogers, et al., *Neurobiology of Aging* 1996, 17, 681–686), Hunting-ton's diseases, prion diseases, myasthenic gravis, and Duchenne's muscular dystrophy, u) pain, v) autoimmune encephalomyelitis (Gijbels, et al., *J. Clin. Invest.* 1994, 94, 2177–2182; A. M. Ramanic, et al., *J. Cell Biology* 1994, 125, 1165–1178) and w) diseases linked to TNFa production and/or signaling such as a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med.* 1988, 319, 397), endotoxic shock (Beutler et al. *Science* 1985, 229, 869; Ashkenasi et al. *Proc. Nat'l. Acad. Sci. USA* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995–6, 47, 97) including Crohn's disease (van Deventer et al. *Aliment. Pharmacol. Therapeu.* 1996, 10 (*Suppl.* 2), 107; van Dullemen et al. *Gastroenterology* 1995, 109, 129) and ulcerative colitis (Masuda et al. *J. Clin. Lab. Immunol.* 1995, 46, 111), Jarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taverne et al. *Parasitol. Today* 1996, 12, 290) including *Plasmodium falciparum* malaria (Perlmann et al. *Infect. Immunit.* 1997, 65, 116) and cerebral malaria (Rudin et al. *Am. J. Pathol.* 1997, 150, 257), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), arteriosclerosis including atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633), host-versus-graft reactions (Piguet et al. *Immunol. Ser.* 1992, 56, 409) including ischemia reperfusion injury (Colletti et al. *J. Clin. Invest.* 1989, 85, 1333) and allograft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86), infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma cruzi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdorferi* (Brandt et al. *Infect. Immunol.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

The need for new therapies is especially important in the case of arthritic diseases. The primary disabling effect of oeteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Biochimica et Biophysica Acta 695 (1983), 177–214; Eur. Respir. J. 7 (1994), 2062–2072; Critical Reviews in Oral Biology and Medicine 4 (1993), 197–250.

Furthermore, it has been shown that inhibition of degradation of extracellular matrix by the native matrix metalloprotease inhibitor TIMP-2 (a protein) arrests cancer growth (Cancer Res. 52, 701–708, 1992) and that TIMP-2 inhibits tumor-induced angiogenesis in experimental systems (Science 248, 1408–1410, 1990). For a review see Annals of the New York Academy of Sciences 1994, 222–232. It was furthermore demonstrated that the synthetic matrix metalloprotease inhibitor batimastat when given intraperitoneally inhibits human colon tumor growth and spread in an orthotopic model in nude mice (Cancer Res. 54, 4726–4728, 1994) and prolongs the survival of mice bearing human ovarian carcinoma xenografts (Cancer Res. 53, 2087–2091, 1993). The use of this and related compounds has been described in WO-A-9321942.

There are a number of patents and patent applications claiming the use of metalloproteinase inhibitors for the retardation of metastatic cancer, promoting tumor regression, inhibiting cancer cell proliferation, slowing or preventing of cartilage loss associated with osteoarthritis or for treatment of other diseases as noted above (e.g. WO-A-9519965, WO-A-9519956, WO-A-9519957, WO-A-9519961, WO-A-9321942, WO-A-9321942, WO-9421625, U.S. Pat. Nos. 4,599,361; 5,190,937; EP 0574 758 A1, published Dec. 22, 1993; EP 026 436 A1 published Aug. 3, 1988; and EP 0520 573 A1, published Dec. 30, 1992). The preferred compounds of these patents have peptide backbones with a zinc complexing group (hydroxamic acid, thiol, carboxylic acid or phosphinic acid) at one end and a variety of side chains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, the compound described in WO-A-9321942, can only be given intraperitoneally.

Some recent patents describe the use of hyroxamic acids with sulfonamide or sulfone moieties as backbones. See, for example WO 9807697, EP 818442 or WO 9749679 (representative structures shown below).

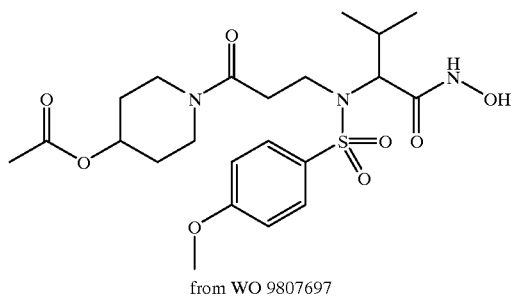

from WO 9807697

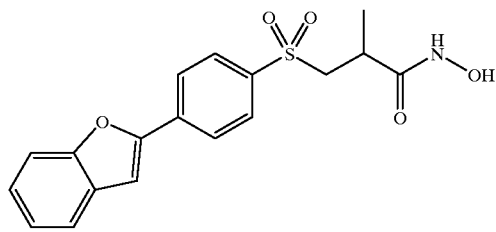

from WO 9749679

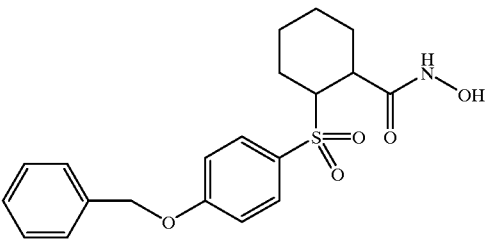

from EP 818442

Matrix metalloprotease inhibitors which are derivatives of butyric and pentanoic acids are disclosed in the following published PCT applications: WO 96/15096, WO 97/43237, WO 97/43240, WO 97/43247, WO 97/43239, WO 97/43245, and WO 97/43238.

SUMMARY

This invention relates to compounds having matrix metalloprotease inhibitory activity and the generalized formula:

$$(T)_x\text{A—B—D—E—G.} \qquad (I)$$

In the above generalized formula (I), $(T)_x$A represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring, designated as the A ring or A unit. When N is employed in conjunction with either S or O in the A ring, these heteroatoms are separated by at least one carbon atom.

The substituent group(s) T are independently selected from the group consisting of halogen; alkyl; haloalkyl; haloalkoxy; alkenyl; alkynyl; —$(CH_2)_p$Q in which p is 0 or an integer of 1–4; -alkenyl-Q in which the alkenyl moiety comprises 2–4 carbons; and alkynyl-Q in which the alkynyl moiety comprises 2–7 carbons. Q in the latter three groups is selected from the group consisting of aryl, heteroaryl, —CN, —CHO, —$NO_2$, —$CO_2R^2$, —$OCOR^2$, —$SOR^3$, —$SO_2R^3$, —$CON(R^4)_2$, —$SO_2N(R^4)_2$, —$COR^2$, —$N(R^4)_2$, —$N(R^2)COR^2$, —$N(R^2)CO_2R^3$, —$N(R^2)CON(R^4)_2$, —$CHN_4$, —$OR^4$, and —$SR^4$.

In these formulae $R^2$ represents H, alkyl, aryl, heteroaryl, arylalkyl, or heteroaryl-alkyl. R3 represents alkyl, aryl, heteroaryl, arylalkyl, or heteroarylalkyl. $R^4$ represents H; alkyl; aryl; heteroaryl; arylalkyl; heteroaryl-alkyl; alkenyl; alkynyl; alkyleneoxy, polyalkyleneoxy, alkylenethio or alkyleneamino terminated with H, alkyl, or phenyl; haloalkyl; lower alkoxycarbonyl; or acyl. When two $R^4$ groups are situated on a nitrogen, they may be joined by a bond to form a heterocycle, such as, for example, a morpholine, thiomorpholine, pyrrolidine, or piperidine ring.

Unsaturation in a moiety which is attached to Q or which is part of Q is separated from any N, O, or S of Q by at least one carbon atom. The A ring may be unsubstituted or may carry up to 2 substituents T. Accordingly, the subscript x is 0, 1, or 2.

In the generalized formula (I), B represents a bond or an optionally substituted aromatic 6-membered ring or a heteroaromatic 5–6 membered ring containing 1–2 atoms of N, O, or S. When B is a ring, it is referred to as the B ring or B unit. When N is employed in conjunction with either S or O in the B ring, these heteroatoms are separated by at least one carbon atom. There may be 0–2 substituents T on ring B.

In the generalized formula (I), D represents

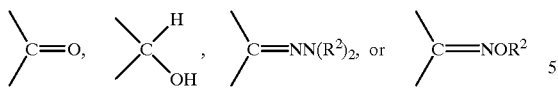

in which R² is defined as above and each R² may be the same or different.

In the generalized formula (I), E represents a chain of n carbon atoms bearing m substituents R⁶, in which the R⁶ groups are independent substituents, or constitute spiro or nonspiro rings. Rings may be formed in two ways: a) two groups R⁶ are joined, and taken together with the chain atom(s) to which the two R6 group(s) are attached, and any intervening chain atoms, constitute a 3–7 membered ring, or b) one group R⁶ is joined to the chain on which this one group R⁶ resides, and taken together with the chain atom(s) to which the R⁶ group is attached, and any intervening chain atoms, constitutes a 3–7 membered ring. The number n of carbon atoms in the chain is 2 or 3, and the number m of R⁶ substituents is an integer of 1–3.

Each group R⁶ is independently selected from the group consisting of:
  fluorine;
  hydroxyl, with the proviso that a single carbon atom may bear no more than one hydroxyl group;
  alkyl;
  aryl;
  heteroaryl;
  arylalkyl;
  heteroaryl-alkyl;
  alkenyl;
  aryl-substituted alkenyl;
  heteraryl-substituted alkenyl;
  alkynyl;
  aryl-substituted alkynyl;
  heteroaryl-substituted alkynyl;
  —(CH₂)ₜR⁷, wherein t is 0 or an integer of 1–5 and R⁷ is selected from the group consisting of:
    N-phthalimidoyl;
    N-(1,2-naphthalenedicarboximidoyl);
    N-(2,3-naphthalenedicarboximidoyl);
    N-(1,8-naphthalenedicarboximidoyl);
    N-indoloyl;
    N-(2-pyrrolodinonyl);
    N-succinimidoyl;
    N-maleimidoyl;
    3-hydantoinyl;
    1,2,4-urazolyl;
    amido;
    urethane;
    urea; and
    nonaromatic substituted or unsubstituted heterocycles containing and connected through a N atom, and comprising one or two additional N, O, S, SO, or SO₂, and containing zero, one or two carbonyls, and optionally bearing a fused benzene or pyridine ring; and
    amino;
    and corresponding heteroaryl moieties in which the aryl portion of an aryl-containing R⁷ group comprises 4–9 carbons and at least one N, O, or S heteroatom; and
  —(CH₂)ᵥZR⁸ in which v is 0 or an integer of 1–4, Z represents

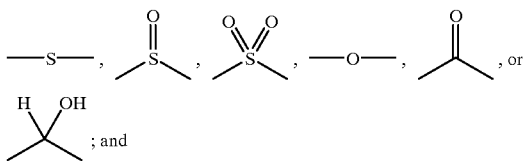

R⁸ is selected from the group consisting of:
  alkyl;
  aryl;
  heteroaryl;
  arylalkyl;
  heteroaryl-alkyl; and
  —C(O)R⁹ in which R⁹ represents alkyl of at least two carbons, aryl, heteroaryl, arylalkyl, or heteroaryl-alkyl;
and with the further provisos that
  when R⁸ is —C(O)R⁹, Z is S or O;
  when Z is O, R⁸ may also be alkyleneoxy or polyalkyleneoxy terminated with H, alkyl, or phenyl; and
  trialkylsilyl-substituted alkyl.

Furthermore, aryl or heteroaryl portions of any of the T or R⁶ groups optionally may bear up to two substituents selected from the group consisting of —(CH₂)ᵧC(R⁴)(R³)OH, —(CH₂)ᵧOR⁴, —(CH₂)ᵧSR⁴, —(CH₂)ᵧS(O)R⁴, —(CH₂)ᵧS(O)₂R⁴, —(CH₂)ᵧSO₂N(R⁴)₂, —(CH₂)ᵧN(R⁴)₂, —(CH₂)ᵧN(R⁴)COR¹², —OC(R⁴)₂O— in which both oxygen atoms are connected to the aryl ring, —(CH₂)ᵧCOR⁴, —(CH₂)ᵧCON(R⁴)₂, —(CH₂)ᵧCO₂R⁴, —(CH₂)ᵧOCOR⁴, -halogen, —CHO, —CF₃, —NO₂, —CN, and —R³, in which y is 0–4. R³ and R⁴ are defined as above; in addition, any two R⁴ which are attached to one nitrogen may be joined to form a heterocycle such as morpholine, thiomorpholine, pyrrolidine, or a piperidine ring.

In the generalized formula (I), G represents

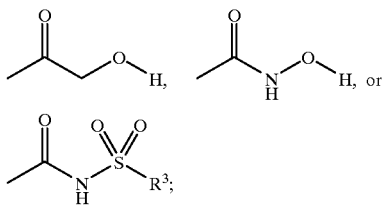

in which R³ is defined as above; and with the proviso that when G is

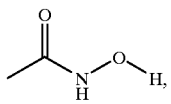

each R⁶ is an independent substituent. Pharmaceutically acceptable salts of these compounds as well as commonly used prodrugs of these compounds such as O-acyl derivatives of invention compounds which contain hydroxy groups are also within the scope of the invention.

In most related reference compounds of the prior art, the biphenyl portion of the molecule is unsubstituted, and the propanoic or butanoic acid portion is either unsubstituted or has a single methyl or phenyl group. Presence of the larger phenyl group has been reported to cause prior art compounds to be inactive as anti-inflammatory analgesic agents. See, for example, R. G. Child, et al., J. Pharm. Sci., 6, 466–476 (1977) By contrast, it has now been found that compounds which exhibit potent MMP inhibitory activity contain a substituent of significant size on the propanoic or butanoic portion of the molecule. The biphenyl portions of the best MMP inhibitors also preferably contain a substituent on the 4' position, although when the propanoic or butanoic portions are optimally substituted, the unsubstituted biphenyl compounds of the invention have sufficient activity to be considered realistic drug candidates.

In addition to the above-described compounds, the invention also relates to pharmaceutical compositions having matrix metalloprotease inhibitory activity, which compositions comprise a compound of the invention as described above and in more detail in the detailed description below, and a pharmaceutically acceptable carrier.

The invention also relates to a method of treating a mammal such as a human, a farm animal, or a domestic pet, to achieve an effect, in which the effect is: alleviation of osteoarthritis; alleviation of rheumatoid arthritis; alleviation of septic arthritis; alleviation of autoimmune disease; alleviation of autoimmune encephalomyelitis; alleviation of periodontal disease; alleviation of corneal ulceration; alleviation of proteinuria; alleviation of aneurysmal aortic disease; alleviation of dystrophobic epidermolysis bullosa; alleviation of diseases of abnormal bone loss including osteoporosis; alleviation of tempero mandibular joint disease; alleviation of demyelinating diseases of the nervous system including multiple sclerosis; alleviation of chronic obstructive pulmonary disease; alleviation of acute and chronic neurodegenerative disorders including stroke, spinal cord and traumatic brain injury, amyotrophic lateral sclerosis, cerebral amyloid angiopathy, CNS injumies in AIDS, Parkinson's disease, Alzheimer's disease, Huntington's diseases, prion diseases, myasthenic gravis, and Duchenne's muscular dystrophy; alleviation of cardiovascular and pulmonary diseases including atherosclerosis, thrombotic events, atheroma, hemodynamic shock, unstable angina, restenosis, heart failure, and chronic obstructive pulmonary disease; alleviation of decubital ulcers; alleviation of aneurysmal diseases including those of the aorta, heart or brain; alleviation of metabolic diseases including diabetes and obesity mediated by insulin resistance, macular degeneration and diabetic retinopathy mediated by agiogenesis; alleviation of cachexia; alleviation of premature skin aging; alleviation of diseases linked to TNFα production including acute rheumatic fever, bone resorption, sepsis, gram negative sepsis, septic shock, endotoxic shock, toxic shock syndrome, systemic inflammatory response syndrome, inflammatory bowel diseases including Crohn's disease and ulcerative colitis, Jarisch-Herxheimer reactions, asthma, adult respiratory distress syndrome, acute pulmonary fibrotic diseases, pulmonary sarcoidosis, allergic respiratory diseases, silicosis, coal worker's pneumoconiosis, alveolar injury, hepatic failure, liver disease during acute inflammation, severe alcoholic hepatitis, malaria including *Plasmodium falciparum* malaria and cerebral malaria, congestive heart failure, damage following heart disease, arteriosclerosis including atherosclerosis, Alzheimer's disease, acute encephalitis, brain injury, pancreatitis including systemic complications in acute pancreatitis, impaired wound healing in infection inflammation and cancer, myelodysplastic syndromes, systemic lupus erythematosus, biliary cirrhosis, bowel necrosis, psoriasis, radiation injury, toxicity following administration of monoclonal antibodies, host-versus-graft reactions including ischemia reperfusion injury and allograft rejections, complications due to total hip replacement, tuberculosis, *Helicobacter pylori* infection during peptic ulcer disease, Chaga's disease resulting from *Trypanosoma cruzi* infection, effects of Shiga-like toxin resulting from *E. coli* infection, the effects of enterotoxin A resulting from Staphylococcus infection, meningococcal infection, *Borrelia burgdorferi* infections, *Treponema pallidum* infections, cytomegalovirus infections, influenza infections, Sendai infections, Theiler's encephalomyelitis, and human immunodeficiency virus infections; retardation of tumor metastasis; retardation of tumor growth or angiogenesis associated with tumor growth; retardation of degenerative cartilage loss following traumatic joint injury; reduction of pain; reduction of coronary thrombosis from atherosclerotic plaque rupture; improved birth control; or improved wound repair including that due to burns; the method comprising administering an amount of a compound of the invention as described above, and in more detail in the detailed description below, which is effective to inhibit the activity of at least one matrix metalloprotease, or inhibit the production of TNFα, or both, in the mammal, resulting in achievement of the desired effect.

DETAILED DESCRIPTION

More particularly, the compounds of the present invention are materials having matrix metalloprotease inhibitory activity and the generalized formula:

$$(T)_xA—B—D—E—G \quad (I)$$

in which $(T)_xA$ represents a substituted or unsubstituted aromatic or heteroaromatic moiety selected from the group consisting of:

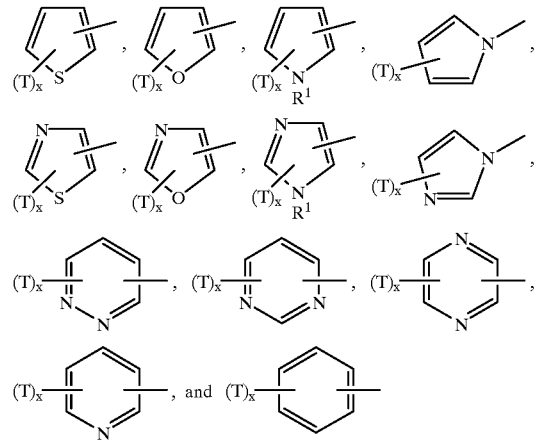

in which $R^1$ represents H or alkyl of 1–3 carbons.

In these structures, the aromatic ring is referred to as the A ring or A unit, and each T represents a substituent group, referred to as a T group or T unit. Substituent groups T are independently selected from the group consisting of: the halogens —F, —Cl, —Br, and —I; alkyl of 1–10 carbons; haloalkyl of 1–10 carbons; haloalkoxy of 1–10 carbons; alkenyl of 2–10 carbons; alkynyl of 2–10 carbons; —(CH$_2$)$_p$Q in which p is 0 or an integer 1–4; -alkenyl-Q in which the alkenyl moiety comprises 2–4 carbons; and -alkynyl-Q in which the alkynyl moiety comprises 2–7 carbons. Q in each of the latter three groups is selected from the group consisting of aryl of 6–10 carbons; heteroaryl comprising 4–9 carbons and at least one N, O, or S heteroatom; —CN; —CHO; —NO$_2$; —CO$_2$R$^2$; —OCOR$^2$; —SOR$^3$; —SO$_2$R$^3$;

—CON(R⁴)₂; —SO₂N(R⁴)2; —C(O)R²; —N(R⁴)₂; —N(R²)COR²; —N(R²)CO₂R³; —N(R²)CON(R⁴)₂; —CHN₄; —OR⁴; and —SR⁴. The groups R², R³, and R⁴ are defined as follows.

R² represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R³ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R⁴ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —(C$_q$H$_{2q}$O)$_r$R⁵ in which q is 1–3, r is 1–3, and R⁵ is H provided q is greater than 1, or R⁵ is alkyl of 1–4 carbons, or phenyl; alkylenethio terminated with H, alkyl of 1–4 carbons, or phenyl; alkyleneamino terminated with H, alkyl of 1–4 carbons, or phenyl; —(CH₂)$_s$X in which s is 1–3 and X is halogen; —C(O)OR²; or —C(O)R².

When two R⁴ groups are situated on a nitrogen, they may be joined by a bond to form a heterocycle, such as, for example, a morpholine, thiomorpholine, pyrrolidine, or piperidine ring.

Any unsaturation in a moiety which is attached to Q or which is part of Q is separated from any N, O, or S of Q by at least one carbon atom, and the number of substituents, designated x, is 0, 1, or 2.

In the generalized formula (I), B represents a bond or an optionally substituted aromatic or heteroaromatic ring selected from the group consisting of:

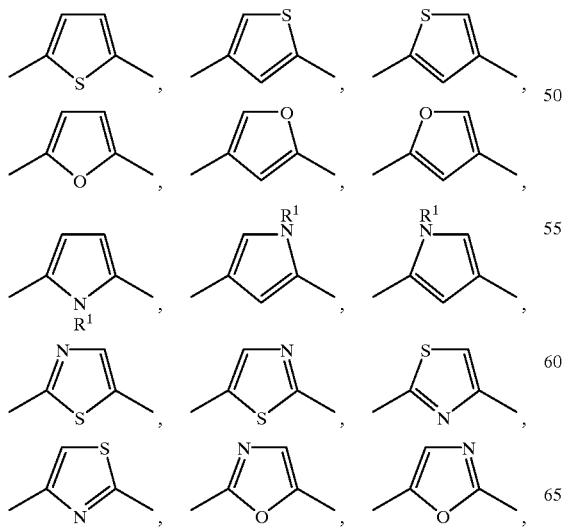

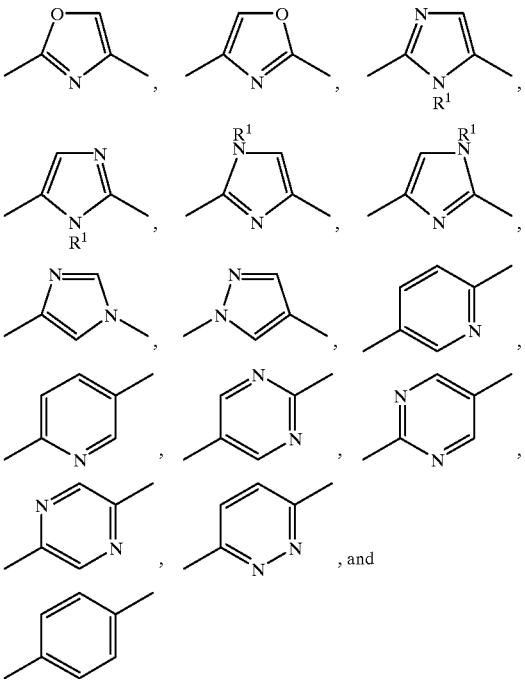

in which R¹ is defined as above. These rings are referred to as the B ring or B unit. There may be 0–2 substituents T on the B ring, T being defined as above.

In the generalized formula (I), D represents the moieties

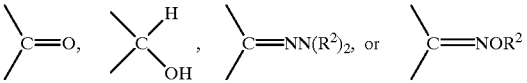

in which R² is defined as above and each R² may be the same or different.

In the generalized formula (I), E represents a chain of n carbon atoms bearing m substituents R⁶, referred to as R⁶ groups or R⁶ units. The R⁶ groups are independent substituents, or constitute spiro or nonspiro rings. Rings may be formed in two ways: a) two groups R⁶ are joined, and taken together with the chain atom(s) to which the two R6 group(s) are attached, and any intervening chain atoms, constitute a 3–7 membered ring, or b) one group R⁶ is joined to the chain on which this one group R⁶ resides, and taken together with the chain atom(s) to which the R⁶ group is attached, and any intervening chain atoms, constitutes a 3–7 membered ring. The number n of carbon atoms in the chain is 2 or 3, and the number m of R⁶ substituents is an integer of 1–3.

Each group R⁶ is independently selected from the group consisting of the substituents listed below as items 1)–16).

1) fluorine;
2) hydroxyl, with the proviso that a single carbon atom may bear no more than one hydroxyl group;
3) alkyl of 1–10 carbons;
4) aryl of 6–10 carbons;
5) heteroaryl comprising 4–9 carbons and at least one N, O, or S heteroatom;
6) arylalkyl in which the aryl portion contains 6–10 carbons and the alkyl portion contains 1–8 carbons;
7) heteroaryl-alkyl in which the heteroaryl portion comprises 4–9 carbons and at least one N, O, or S heteroatom, and the alkyl portion contains 1–8 carbons;

8) alkenyl of 2–10 carbons;
9) aryl-alkenyl in which the aryl portion contains 6–10 carbons and the alkenyl portion contains 2–5 carbons;
10) heteroaryl-alkenyl in which the heteroaryl portion comprises 4–9 carbons and at least one N, O, or S heteroatom and the alkenyl portion contains 2–5 carbons;
11) alkynyl of 2–10 carbons;
12) aryl-alkynyl in which the aryl portion contains 6–10 carbons and the alkynyl portion contains 2–5 carbons;
13) heteroaryl-alkynyl in which the heteroaryl portion comprises 4–9 carbons and at least one N, O, or S heteroatom and the alkynyl portion contains 2–5 carbons;
14) —(CH$_2$)$_t$R$^7$ in which t is 0 or an integer of 1–5 and R$^7$ is selected from the group consisting of

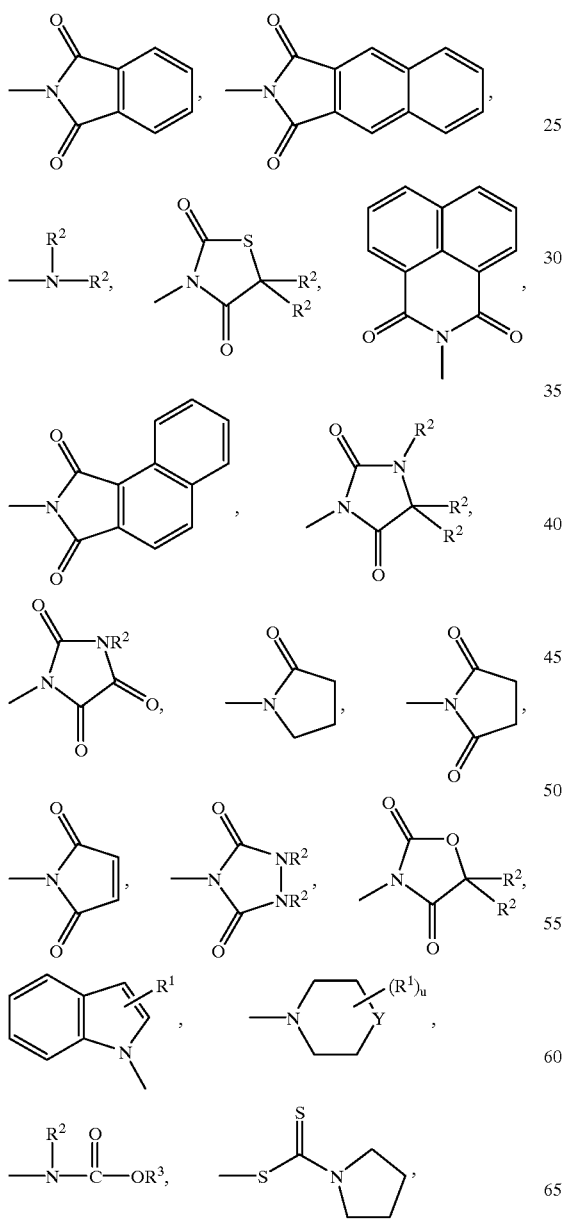

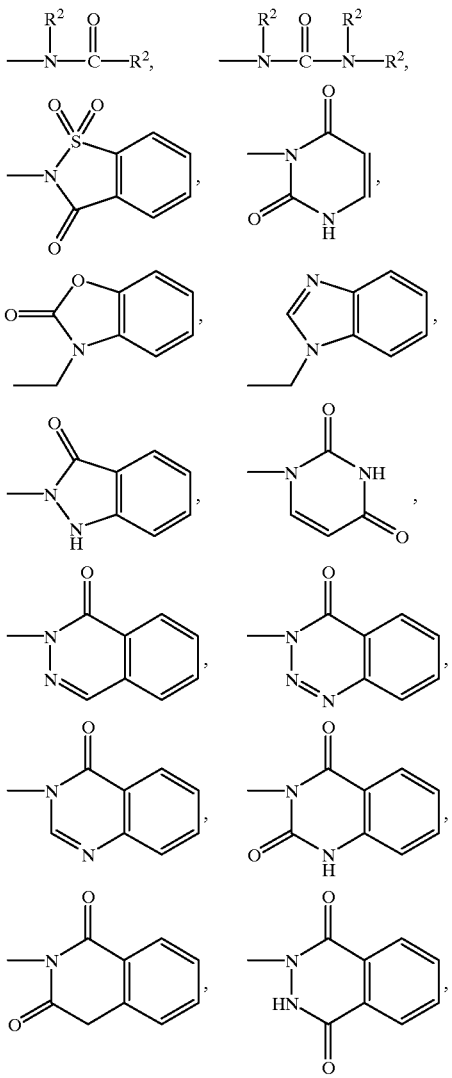

as well as corresponding heteroaryl moieties in which the aryl portion of an aryl-containing R$^7$ group comprises 4–9 carbons and at least one N, O, or S heteroatom. In such R7 groups, Y represents O or S; R$^1$, R$^2$, and R$^3$ are as defined above; and u is 0, 1, or 2;

15) —(CH$_2$)$_v$ZR$^8$ in which v is 0 or an integer of 1 to 4; Z represents —S—, —S(O)—, —SO$_2$—, —O—, carbonyl, or —CH(OH)—; and R$^8$ is selected from the group consisting of: alkyl of 1 to 12 carbons; aryl of 6 to 10 carbons; heteroaryl comprising 4–9 carbons and at least one N, O, or S heteroatom; arylalkyl in which the aryl portion contains 6 to 12 carbons and the alkyl portion contains 1 to 4 carbons; heteroaryl-alkyl in which the aryl portion comprises 4–9 carbons and at least one N, O, or S heteroatom and the alkyl portion contains 1–4 carbons; —C(O)R$^9$ in which R$^9$ represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons, with the provisos that
when R$^8$ is —C(O)R$^9$, Z is —S— or —O—;

when Z is —O—, $R^8$ may also be —$(C_qH_{2q}O)_rR^5$ in which q, r, and $R^5$ are as defined above;

16) —$(CH_2)_wSi(R^{10})_3$ in which w is an integer of 1 to 3, and $R^{10}$ represents alkyl of 1 to 2 carbons.

In addition, aryl or heteroaryl portions of any of the T or $R^6$ groups optionally may bear up to two substituents selected from the group consisting of —$(CH_2)_yC(R^4)(R^3)$OH, —$(CH_2)_yOR^4$, —$(CH_2)_ySR^4$, —$(CH_2)_yS(O)R^4$, —$(CH_2)_yS(O)_2R^4$, —$(CH_2)_ySO_2N(R^4))_2$, —$(CH_2)_yN(R^4))_2$, —$(CH_2)_yN(R^4))COR^3$, —$OC(R^4))_2O$— in which both oxygen atoms are connected to the aryl ring, —$(CH_2)_yCOR^4$, —$(CH_2)_yCON(R^4))_2$, —$(CH_2)_yCO_2R^4$, —$(CH_2)_yOCOR^4$), -halogen, —CHO, —$CF_3$, —$NO_2$, —CN, and —$R^3$, in which y is 0–4; $R^3$ is defined as above; $R^4$ is defined as above and in addition, any two $R^4$ which are attached to one nitrogen may be joined to form a heterocycle, such as a morpholine, thiomorpholine, pyrrolidine, or piperidine ring.

In the generalized formula (I), G represents

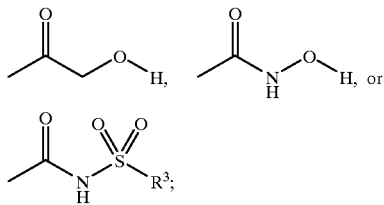

in which $R^3$ is defined as above; and with the proviso that when G is

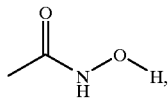

each $R^6$ is an independent substituent. Pharmaceutically acceptable salts of these compounds as well as commonly used prodrugs of these compounds such as O-acyl derivatives of these compounds are also within the scope of the invention.

In the compounds of the invention, the following are preferred.

The substituent group T, when it is on the ring A, is preferably halogen, 1-alkynyl-Q, or an ether $OR^4$ wherein $R^4$ is preferably alkyl of 1–12 carbons or arylalkyl in which the aryl portion is 6–10 carbons and the alkyl portion contains 1–4 carbons. Most preferably, T is halogen, or —C≡C—$(CH_2)_tOH$ in which t is an integer of 1–5, and when T is $OR^4$, $R^4$ is alkyl of 1–6 carbons, or benzyl.

The subscript x, which defines the number of T substituents, is preferably 1 or 2, most preferably 1, and this substituent T is preferably on the 4-position of ring A.

The A ring is preferably a phenyl or thiophene ring, most preferably phenyl. The A ring preferably bears at least one substituent group T, preferably located on the position furthest from the position of the A ring which is connected to the B ring.

The B moiety of generalized formula (I) is a bond or a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such groups may be moieties such as lower alkyl, lower alkoxy, CN, $NO_2$, halogen, etc., but are not to be limited to such groups. The B moiety is preferably a 1,4-phenylene or 2,5-thiophene ring, most preferably 1,4-phenylene.

The D unit is most preferably a carbonyl or a —CHOH— group.

The group R6 is preferably:

1) arylalkyl wherein the aryl portion contains 6–10 carbons and the alkyl portion contains 1–8 carbons;
2) —$(CH_2)_tR^7$ wherein t is 0 or an integer of 1–5 and $R^7$ is an imidoyl group fused to an aromatic residue, or the 1,2,3-benzotriazin-4(3H)-one-3-yl group; or
3) —$(CH_2)_vZR^8$ wherein v is 0 or an integer of 1–4, Z is S or O, and $R^8$ is aryl of 6–10 carbons or arylalkyl wherein the aryl portion contains 6 to 12 carbons and the alkyl portion contains 1 to 4 carbons.

The group R6 is most preferably one of the following, and in these, any aromatic moiety is preferably substituted:

1) arylalkyl wherein the aryl portion is phenyl and the alkyl portion contains 1–4 carbons;
2) —$(CH_2)_tR^7$ wherein t is an integer of 1–3, and $R^7$ is N-phthalimidoyl, 1,2,3-benzotriazin-4(3H)-one-3-yl, N-(1,2-naphthalenedicarboximidoyl), N-(2,3-naphthalenedicarboximidoyl), or N-(1,8-naphthalenedicarboximidoyl); or
3) —$(CH_2)_vZR^8$ wherein v is an integer of 1–3, Z is S, and $R^8$ is phenyl.

The G unit is most preferably a hydroxamic acid group.

It is to be understood that as used herein, the term "alkyl" means straight, branched, cyclic, and polycyclic materials. The term "haloalkyl" means partially or fully halogenated alkyl groups such as —$(CH_2)_2Cl$, —$CF_3$ and —$C_6F_{13}$, for example.

In one of its embodiments, the invention relates to compounds of generalized formula (I) in which at least one of the units A, B, T, and $R^6$ comprises a heteroaromatic ring. Preferred heteroaromatic ring-containing compounds are those in which the heteroaryl groups are heteroaryl of 4–9 carbons comprising a 5–6 membered heteroaromatic ring containing O, S, or $NR^1$ when the ring is 5-membered, and N when said ring is 6-membered. Particularly preferred heteroaromatic ring-containing compounds are those in which at least one of the A and B units comprises a thiophene ring. When A unit is thiophene, it is preferably connected to B unit at position 2 and carries one substituent group T on position 5. When B Unit is thiophene, it is preferably connected through positions 2 and 5 to D and A units respectively.

In another embodiment, the invention relates to compounds of generalized formula (I), in the E unit of which n is 2 and m is 1. These compounds thus possess two carbon atoms between the D unit and the G unit, and carry one substituent on this two-carbon chain.

In another of its embodiments, the invention relates to compounds of generalized formula (I) in which the A ring is a substituted or unsubstituted phenyl group, the B ring is p-phenylene, and aryl portions of any aryl-containing T and $R^6$ moieties contain only carbon in the rings. These compounds thus contain no heteroaromatic rings.

In another of its embodiments, the invention relates to compounds of generalized formula (I) in which m is 1 and $R^6$ is an independent substituent. These compounds are materials which contain only a single substituent $R^6$ on the E unit, and this substituent in not involved in a ring. Preferred compounds within this subset have the formula

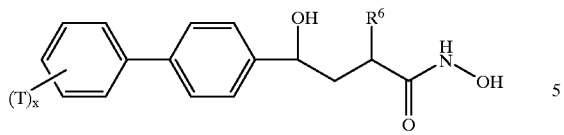

in which x is 1 or 2, and one substituent group T is located on the 4-position of the A ring, relative to the point of attachment between the A and B rings. Substituent group T of this subset is preferably the halogens —Cl, —Br or I or is an ether —OR$^4$. Most preferred compounds contain only one substituent T on the 4-position of the A ring relative to the attachment to B ring.

Preferred compounds of general formula (I) in which R$^6$ is —(CH$_2$)$_t$R$^7$ have t as an integer of 1–5. Preferred compounds of general formula (I) in which R$^6$ is —(CH$_2$)$_v$ZR$^8$ have v as an integer of 1–4 and Z as —S— or —O—. Preferred compounds of general formula (I) in which R$^6$ is alkyl contain 4 or more carbons in said alkyl and those in which R$^6$ is arylalkyl contain 2–3 carbons in the alkyl portion of said arylalkyl.

In another of its embodiments, the invention relates to compounds of generalized formula (I) in which the number of substituents m on the E unit is 2 or 3; and when m is 2, both groups R$^6$ are independent substituents, or together constitute a spiro ring, or one group R$^6$ is an independent substituent and the other constitutes a spiro ring; and when m is 3, two groups R$^6$ are independent substituents and one group R$^6$ constitutes a ring, or two groups R6 constitute a ring and one group R6 is an independent substituent, or three groups R6 are independent substituents. This subset therefore contains compounds in which the E unit is di- or tri-substituted, and in the disubstituted case any rings formed by one or both R$^6$ groups are spiro rings, and in the trisubstituted case, the R$^6$ groups may form either spiro or nonspiro rings.

In another of its embodiments, the invention relates to compounds of generalized formula (I) in which the number of substituents m on the E unit is 1 or 2; and when m is 1, the group R$^6$ constitutes a nonspiro ring; and when m is 2, both groups R$^6$ together constitute a nonspiro ring or one group R6 is an independent substituent and the other constitutes a nonspiro ring. This subset therefore contains compounds in which the E unit carries one or two substituents R$^6$, and at least one of these substituents is involved in a nonspiro ring.

More particularly, representative compounds of generalized formula (I) in which one or more of the substituent groups R$^6$ are involved in formation of nonspiro rings have E units of the following structures:

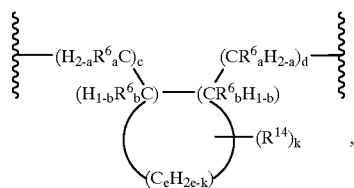

-continued

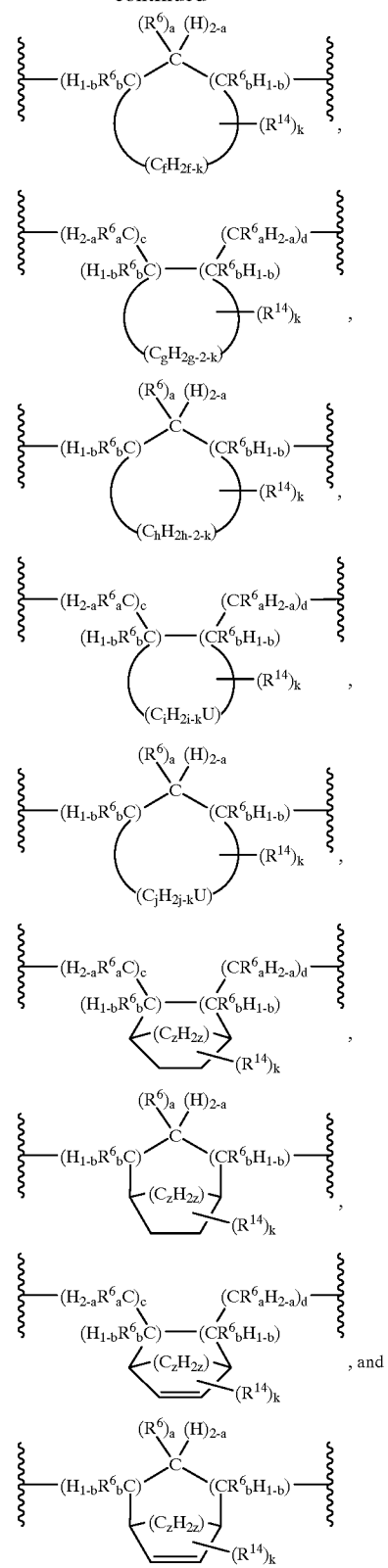

in which a is 0, 1, or 2; b is 0 or 1; c is 0 or 1; d is 0 or 1; c+d is 0 or 1; e is 1–5; f is 1–4; g is 3–5; h is 2–4; i is 0–4; j is 0–3; k is 0–2; the total number of groups R$^6$ is 0, 1, or 2; U represents O, S, or NR$^1$; and z is 1 or 2; Each group R$^{14}$ is independently selected from the group consisting of: alkyl of 1–9 carbons; arylalkyl in which the alkyl portion contains 1–7 carbons and the aryl portion contains 6–10 carbons; alkenyl of 2–9 carbons; aryl-substituted alkenyl in which the alkenyl portion contains 2–4 carbons and the aryl portion contains 6–10 carbons; alkynyl of 2–9 carbons; aryl-substituted alkynyl in which the alkynyl portion contains 2–4 carbons and the aryl portion contains 6–10 carbons; aryl of 6–10 carbons; —$COR^2$; —$CH(OH)R^2$; —$CO_2R^3$; —$CON(R^2)_2$; —$(CH_2)_tR^7$ in which t is 0 or an integer of 1–4; and —$(CH_2)_vZR^8$ in which v is 0 or an integer of 1 to 3, and Z represents —S—, S(O), $SO_2$, or —O—. $R^1$, $R^7$, and $R^8$ have been defined above.

Preferred compounds of generalized formula (I) in which one or more of the substituent groups $R^6$ are involved in formation of nonspiro rings have E units of the following structures:

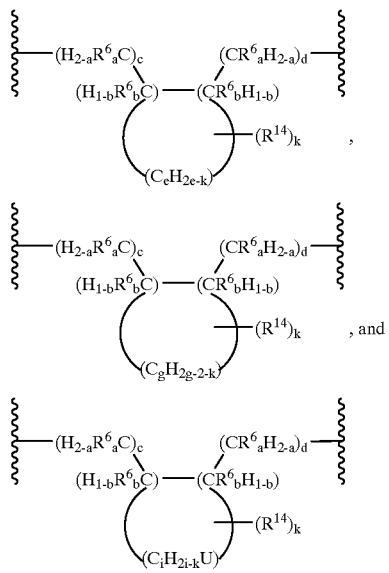

in which a, b, c, d, (c+d), e, g, i, k, the total number of groups $R^6$, U, and $R^{14}$ are as defined above.

The more preferred compounds of generalized formula (I) in which one or more of the substituent groups $R^6$ are involved in formation of nonspiro rings have the formula

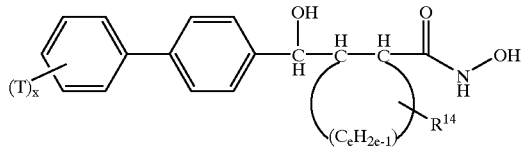

in which the subscript x is 1 or 2; one substituent T is located on the 4-position of the A ring, relative to the point of attachment between the A and B rings; e is 2 or 3; and $R^{14}$ is as defined above.

GENERAL PREPARATIVE METHODS

The compounds of the invention may be prepared by use of known chemical reactions and procedures. Nevertheless, the following general preparative methods are presented to aid the reader in synthesizing the inhibitors, with more detailed particular examples being presented below in the experimental section describing the working examples. General methods A through K may be used to prepare appropriately substituted 4-biaryl-4-oxobutanoic acids, 4-aryl-4-oxobutanoic acids, 5-biaryl-5-oxopentanoic acids, or 5-aryl-5-oxopentanoic acids to be used as key intermediates for the preparation of the compounds of the invention. These general methods are also found in WO 9615096 (May 23, 1996) along with exemplary preparations of the keto acids which are the key intermediates used for preparation of the compounds of the present application. Any one of general methods L through P may then be used to prepare the compounds of this invention from the products of methods A through K. The choice of a specific synthetic method is dictated by the proviso that the conditions used do not effect undesired changes in the T or $R^6$ moieties of the compounds prepared.

All variable groups of these methods are as described in the generic description if they are not specifically defined below. The variable subscript n is independently defined for each method. When a variable group with a given symbol (i.e. $R^6$ or T) is used more than once in a given structure, it is to be understood that each of these groups may be independently varied within the range of definitions for that symbol. As defined above, the compounds of the invention contain as the E unit a chain of 2 or 3 carbon atoms bearing 1 to 3 substituents $R^6$ which are not defined as H. By contrast, it is to be noted that in the general method schemes below, the $R^6$ groups are used as if their definition includes H, to show where such $R^6$ groups may exist in the structures, and for ease in drawing. No change in the definition of $R^6$ is intended by this non-standard usage, however. Thus, only for purposes of the general method schemes below, $R^6$ may be H in addition to the moieties set forth in the definition of $R^6$. The ultimate compounds contain 1 to 3 non-hydrogen groups $R^6$.

General Method A

The key intermediates in which the rings A and B are substituted phenyl and phenylene respectively are conveniently prepared by use of a Friedel-Crafts reaction of a substituted biphenyl II with an activated acyl-containing intermediate such as the succinic or glutaric anhydride derivative III or acid chloride IV in the presence of a Lewis acid catalyst such as aluminum trichloride in an aprotic solvent such as 1,1,2,2-tetrachloroethane. The well known Friedel-Crafts reaction can be carried out with many alternative solvents and acid catalysts as described by E. Berliner, *Org. React.*, 5, 229 (1949) and H. Heaney, *Comp. Org. Synth.*, 2, 733 (1991).

Method A

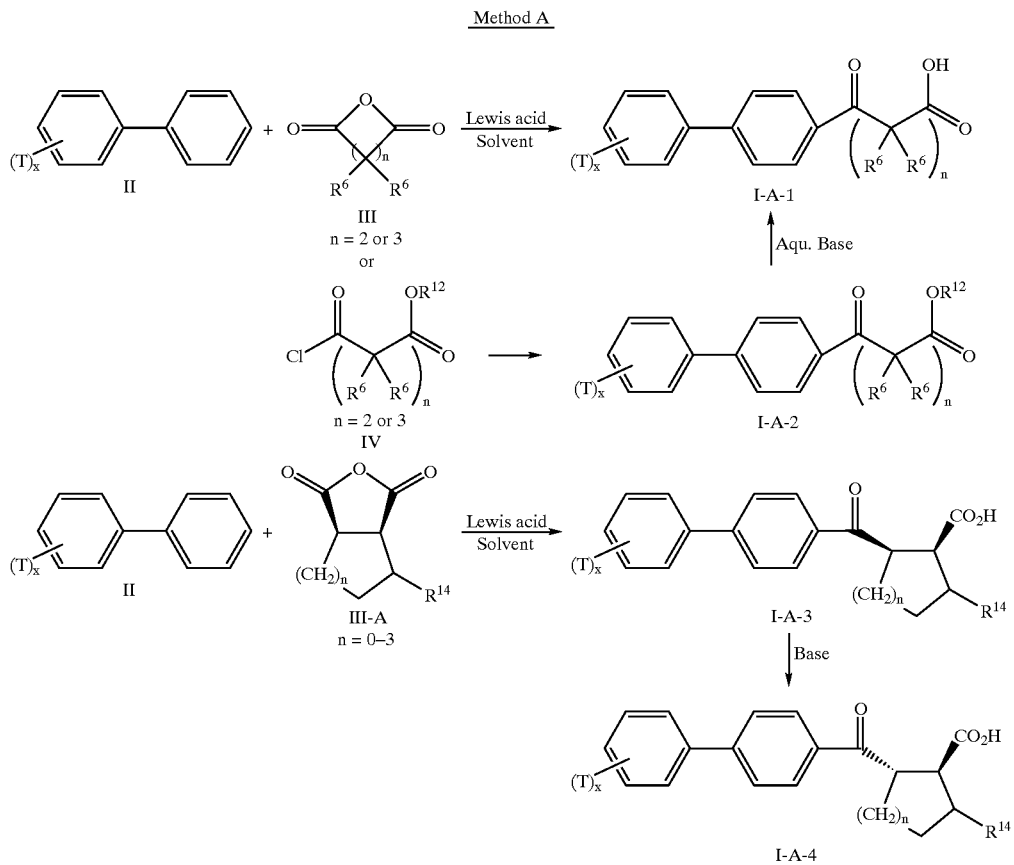

If the anhydride III is monosubstituted or multiply-substituted in an unsymmetrical way, the raw product I-A often exists as a mixture of isomers via attack of the anhydride from either of the two carbonyls. The resultant isomers can be separated into pure forms by crystallization or chromatography using standard methods known to those skilled in the art.

When they are not commercially available, the succinic anhydrides III can be prepared via a Stobbe Condensation of a dialkyl succinate with an aldehyde or ketone (resulting in side chain $R^6$), followed by catalytic hydrogenation, hydrolysis of a hemiester intermediate to a diacid and then conversion to the anhydride III by reaction with acetyl chloride or acetic anhydride. Alternatively, the hemiester intermediate is converted by treatment with thionyl chloride or oxalyl chloride to the acid chloride IV in which $R^{12}$ is lower alkyl. For a review of the Stobbe condensation, including lists of suitable solvents and bases see W. S. Johnson and G. H. Daub, Org. React., 6, 1 (1951). This method, as applied to the preparation of III ($R^6$=H, isobutyl and H, n-pentyl), has been described by D. Wolanin, et al., U.S. Pat. No. 4,771,038, Sep. 13, 1988.

Method A is especially useful for the preparation of cyclic key intermediates such as I-A-3 in which two $R^6$ groups are connected in a methylene chain to form a 4–7 membered ring. Small ring (3–5 member) anhydrides are readily available only as cis isomers which yield cis invention compounds I-A-3. The trans compounds I-A-4 are then prepared by treatment of I-A-3 with a base such as DBU in THF.

The substituted four member ring starting material anhydrides such as III-A-1 are formed in a photochemical 2+2 reaction as shown below. This method is especially useful for the preparation of compounds in which $R^{14}$ is acetoxy or acetoxymethylene. After the subsequent Friedel-Crafts reaction the acetate can be removed by basic hydrolysis and the carboxyl protected by conversion to 2-(trimethylsilyl)ethyl ester. The resultant intermediate with $R^{14}$=CH$_2$OH can be converted to key intermediates with other $R^{14}$ groups by using procedures described in General Method K.

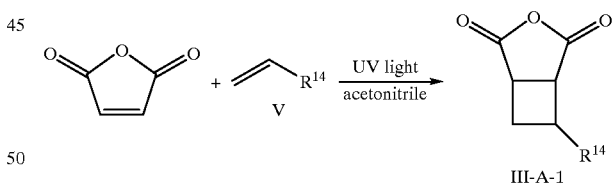

The Friedel Crafts method is also useful when double bonds are found either between C-2 and C-3 of a succinoyl chain (from maleic anhydride or 1-cyclopentene-1,2-dicarboxylic anhydride, for example) or when a double bond is found in a side chain, such as in the use of itaconic anhydride as starting material to yield products in which two $R^6$ groups as found on one chain carbon together form an exo-methylene (=CH$_2$) group. Subsequent uses of these compounds are described in Methods D and E.

General Method B

Alternatively key intermediates can be prepared via a reaction sequence involving mono-alkylation of a dialkyl malonate VI with an alkyl halide to form intermediate VII, followed by alkylation with a halomethyl biphenyl ketone VIII to yield intermediate IX. Compounds of structure IX are then hydrolyzed with aqueous base and then heated to decarboxylate the malonic acid intermediate and yield I-B-2 (Method B-1). By using one equivalent of aqueous base the esters I-B-2 with $R^{12}$ as alkyl are obtained, and using more than two equivalents of base the acid compounds ($R^{12}$=H) are obtained. Optionally, heat is not used and the diacid or or heteroaromatic rings that may participate in intramolecular acylation reactions to give side products if Method A were to be used. This method is also very useful when the $R^6$ group adjacent to the carboxyl of the final compound contains heteroatoms such as oxygen, sulfur, or nitrogen, or more complex functions such as imide rings.

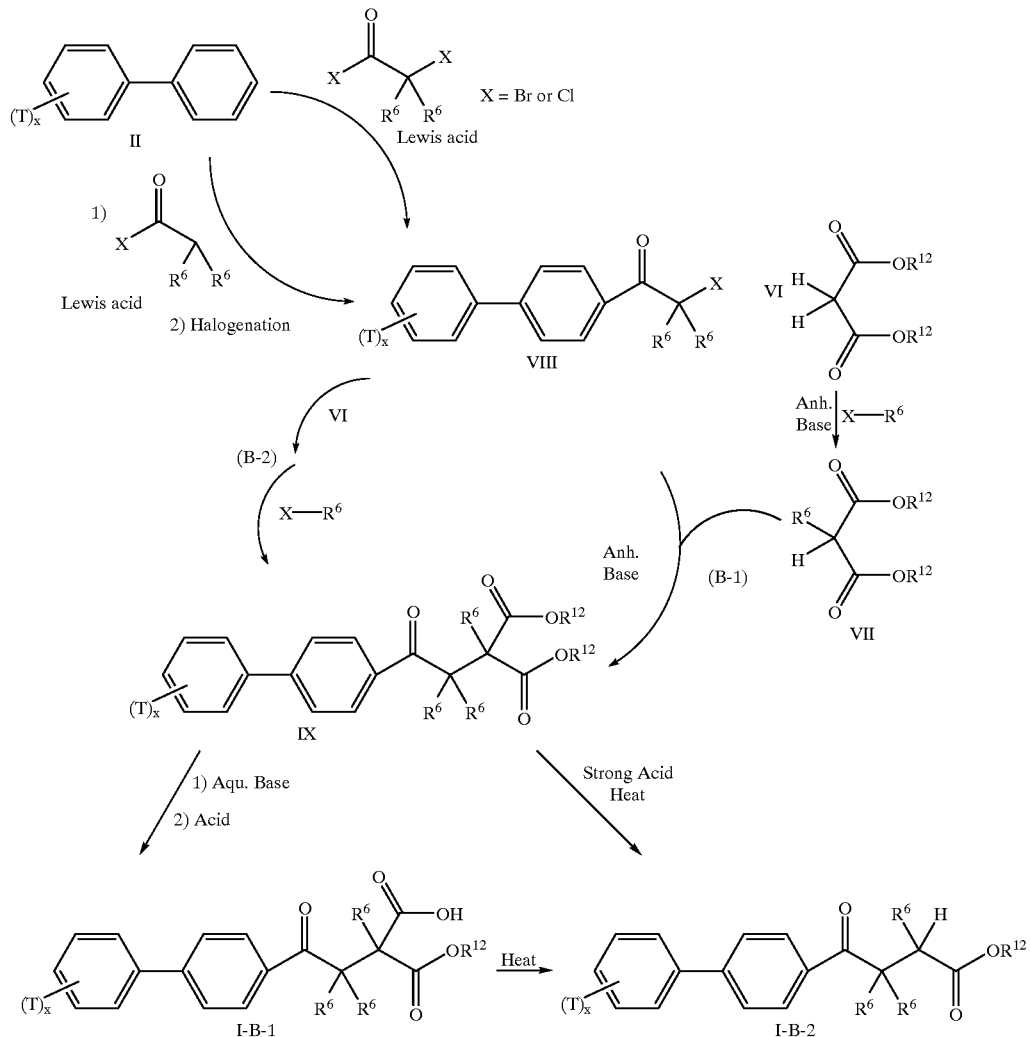

Method B acid-ester I-B-1 is obtained. Alternatively, the diester intermediate IX can be heated with a strong acid such as concentrated hydrochloric acid in acetic acid in a sealed tube at about 110° C. for about 24 hr to yield I-B-2 ($R^{12}$=H).

Alternatively, the reaction of VI with VIII can be conducted before that with the alkyl halide to yield the same IX (Method B-2).

Intermediates VIII are formed from biphenyls II in a Friedel-Craft reaction with haloacetyl halides such as bromoacetyl bromide or chloroacetyl chloride. Alternatively, the biphenyl can be reacted with acetyl chloride or acetic anhydride and the resultant product halogenated with, for example, bromine to yield intermediates VIII (X=Br).

Method B has the advantage of yielding single regio isomers when Method A yields mixtures. Method B is especially useful when the side chains $R^6$ contain aromatic General Method C Especially useful is the use of chiral HPLC to separate the enantiomers of racemic key intermediate mixtures (see, for example, D. Arlt, B. Boemer, R Grosser and W. Lange, Angew. Chem. Int. Ed. Engl. 30 (1991) No. 12). The key intermediates are prepared as pure enantiomers by use of a chiral auxiliary route—see, for example: D. A. Evans, Aldrichimica Acta, 15(2), 23 (1982) and other similar references known to one skilled in the art.

C-1

Acid halide X is reacted with the lithium salt of chiral auxiliary XI (R is often isopropyl or benzyl) to yield intermediate XII, which in turn is alkylated at low temperatures (typically under −50° C.) with halo-tert-butylacetyl compound XIII to yield pure isomer XIV. The use of opposite chirality XI yields opposite chirality XIV. Conversion of XIV to the enantiomerically pure diacid XV is accomplished by treatment with lithium hydroxide/hydrogen peroxide in THF/water, followed by acids such as trifluoroacetic acid. The compound XV is then converted to enantiomerically pure anhydride III-A by treatment with acetyl chloride. The use of a Friedel-Crafts reaction as in method A then converts III-A to I-C-1.

C-2

Biphenyl starting material II may also first be reacted in a Friedel-Crafts reaction as earlier described with succinic anhydride followed by Fisher esterification with a lower alcohol such as methanol in the presence of a strong acid such as sulfuric acid to form acyl derivative I-C-2. The carbonyl group of this material is then blocked as a ketal such as that formed by treatment with 1,2-bistrimethyl-silyloxyethane in the presence of a catalyst such as trimethylsilyltriflate in a suitable solvent. Many other ketal derivatives and reaction conditions familiar to those skilled in the art can also be used in this step. Basic hydrolysis of the ester followed by reaction of the resultant I-C-3 with XI in the presence of an amide coupling agent such as 1-(3-dimethylaminopropyl)-3-ethylcarbodiimide yields amide I-C-4. Reaction of this chiral amide with an alkylating agent such as alkyl or arylalkyl triflate or halide yields enantiomerically enriched product I-C-5 which can be converted to ketal acid I-C-6 by treatment with a weak base such as lithium hydroxide/hydrogen peroxide and then to keto acid I-C-7 by treatment with an acid. These deblocking steps can be conducted in either order.

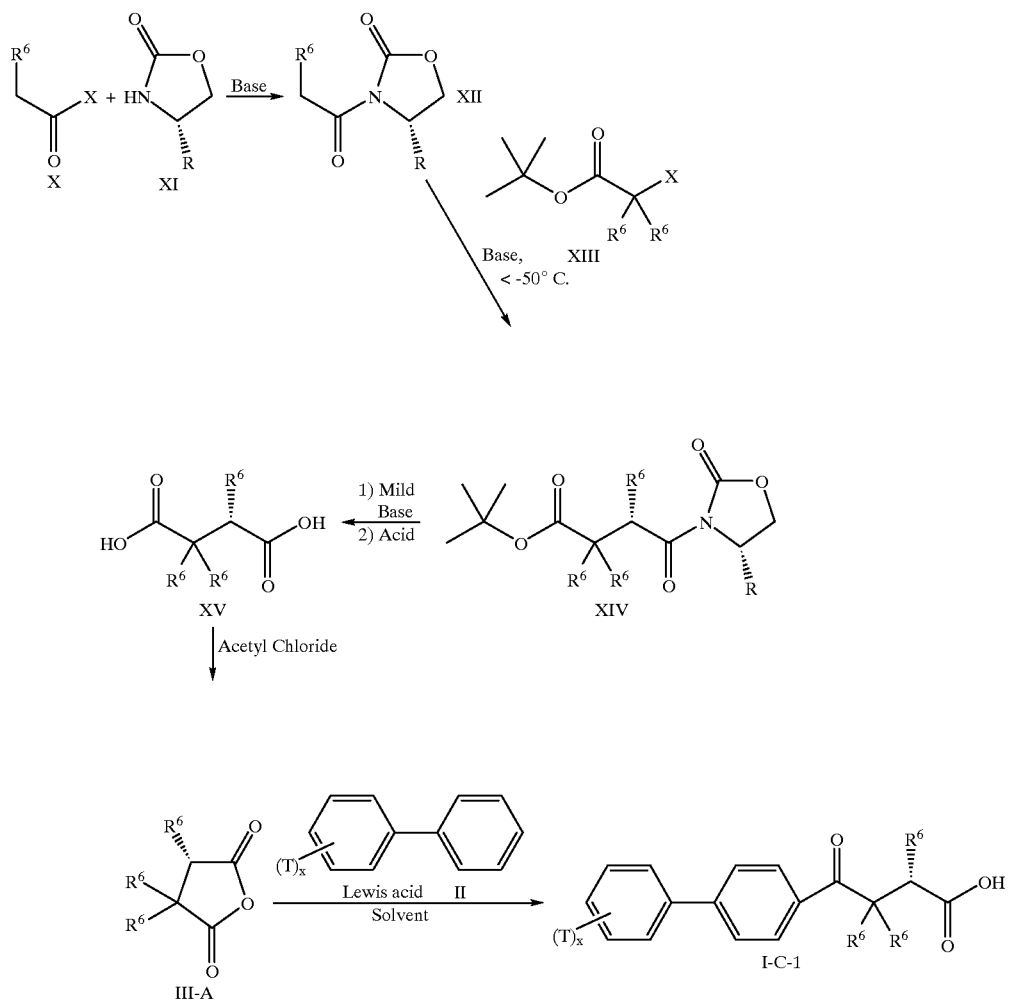

Method C-1

Method C-2

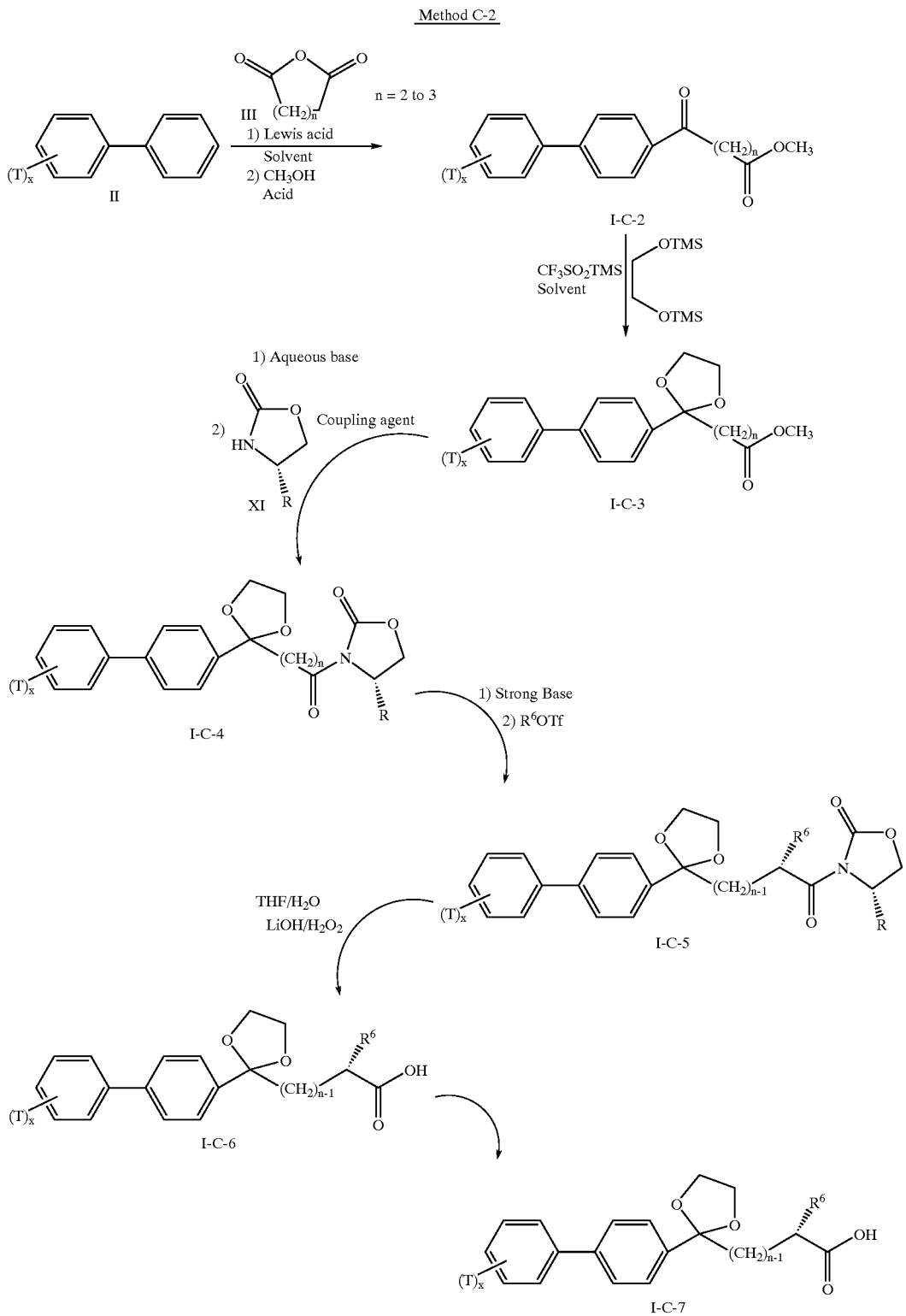

General Method D

Key intermediates in which $R^6$ are alkyl- or aryl- or heteroaryl- or acyl- or heteroarylcarbonyl-thiomethylene are prepared by methods analogous to those described in the patent publication WO 90/05719. Thus substituted itaconic anhydride XVI (n=1) is reacted under Friedel-Crafts conditions to yield acid I-D-1 which can be separated by chromatography or crystallization from small amounts of isomeric I-D-5. Alternatively, I-D-5 are obtained by reaction of key intermediates I-D-4 (from any of Methods A through C) with formaldehyde in the presence of a base.

Compounds I-D-1 or I-D-5 are then reacted with a mercapto derivative XVII or XVIII in the presence of a catalyst such as Potassium carbonate, ethyldiisobutylamine, tetrabutylammonium fluoride or free radical initiators such as azobisisobutyronitrile (AIBN) in a solvent such as dimethylformamide or tetrahydrofuran to yield key intermediates I-D-2, I-D-3, I-D-6 or I-D-7.

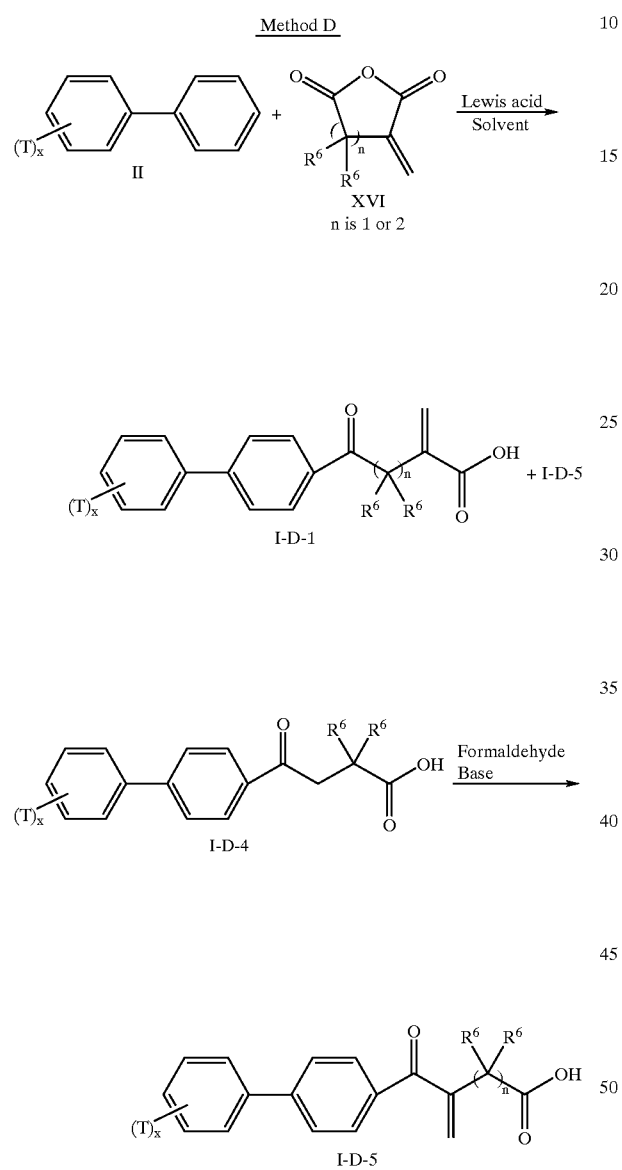

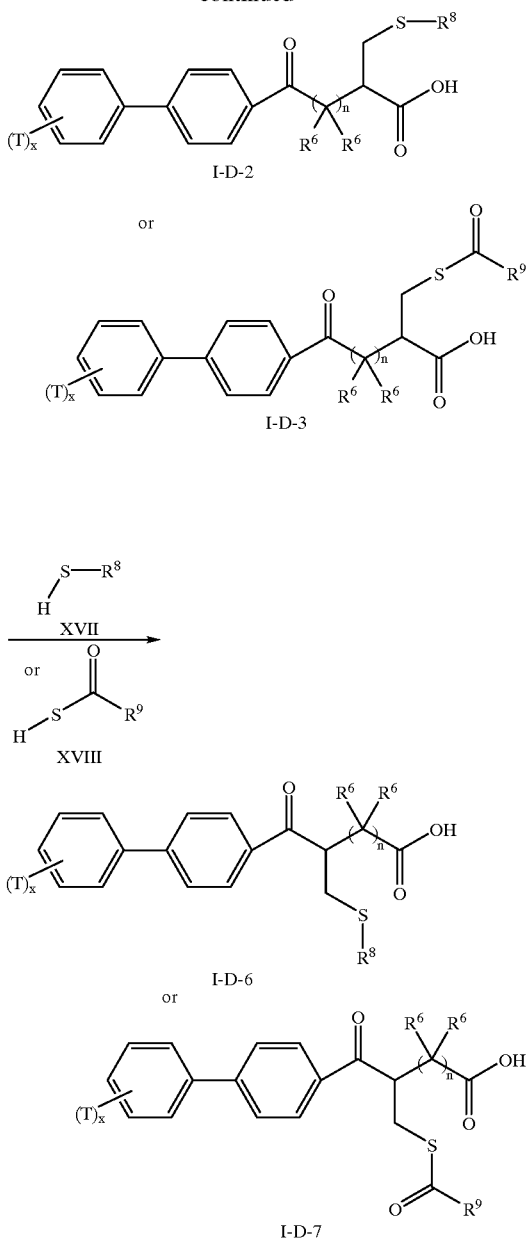

General Method E

Reaction of optionally substituted maleic anhydride XIX under Friedel-Crafts conditions with II yields key intermediate I-E-1, which in turn is reacted with either of mercapto derivatives XVII or XVIII to yield key intermediates I-E-2 or I-E-3, or with substituted amine XX to yield key intermediate I-E-4. Esterification of I-E-1 (R6=H) with $CH_3I$/DBU followed by reagent XXI and AgF and then basic hydrolysis yields pyrrolidine key intermediate I-E-5. $R^{14}$ can be various alkyl or arylalkyl groups including benzyl. Reaction of the intermediate ester (from step 2) with benzyloxycarbonyl chloride in THF at reflux followed by hydrolysis yields key intermediates in which $R^{14}$ is benzyloxycarbonyl.

Method E

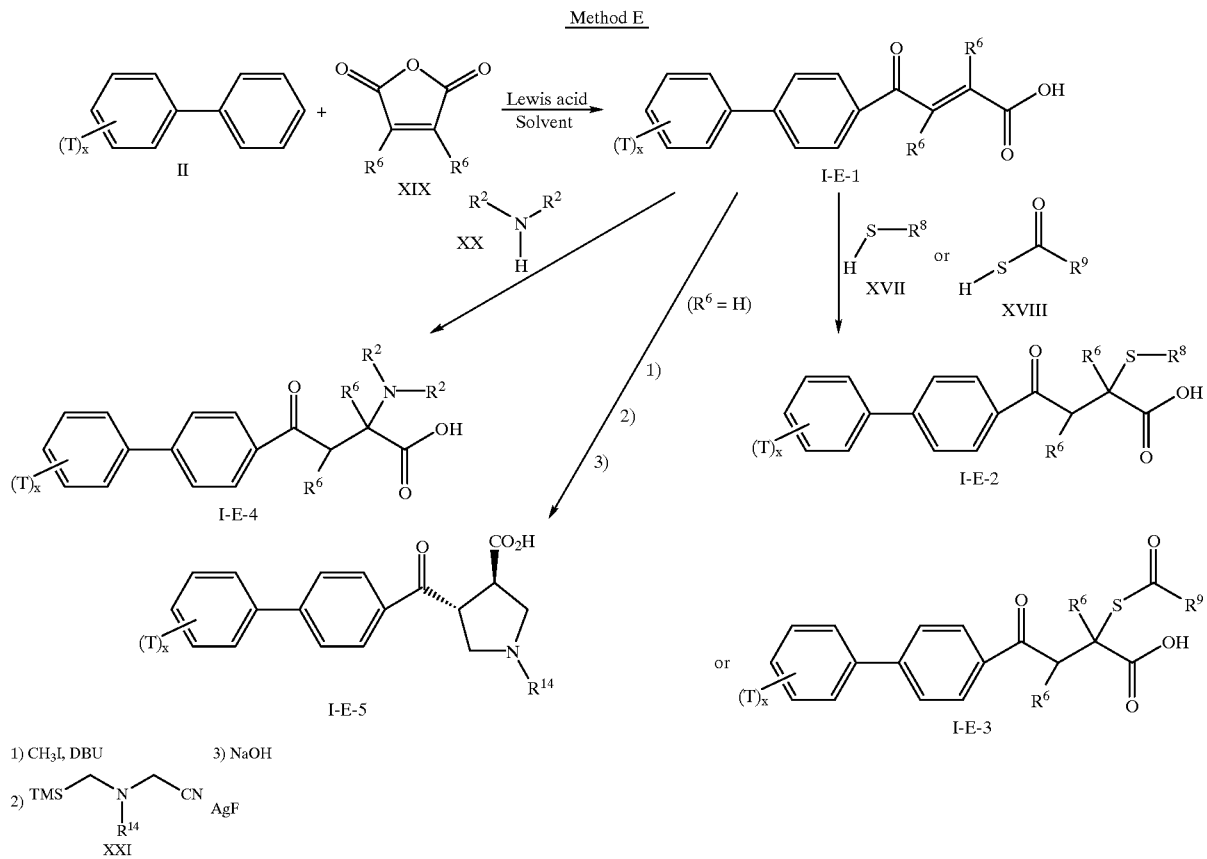

1) $CH_3I$, DBU
2) TMS–N($R^{14}$)–CN, XXI, AgF
3) NaOH

General Method F

Biaryl key intermediates such as those of this application may also be prepared by Suzuki or Stille cross-coupling reactions of aryl or heteroaryl metallic compounds in which the metal is zinc, tin, magnesium, lithium, boron, silicon, copper, cadmium or the like with an aryl or heteroaryl halide or triflate (trifluoromethane-sulfonate) or the like. In the equation below either Met or X is the metal and the other is the halide or triflate. Pd(com) is a soluble complex of palladium such as tetrakis(triphenylphosphine)-palladium (0) or bis-(triphenylphos-phine)-palladium(II) chloride. These methods are well known to those skilled in the art. See, for example, A. Suzuki, Pure Appl. Chem., 66, 213–222 (1994); A. Suzuki, Pure Appl. Chem., 63, 419–422 (1991); and V. Farina and G. Roth, "Metal-Organic Chemistry" Volume 5 (Chapter 1), 1994.

The starting materials XXIII (B=1,4-phenylene) are readily formed using methods analogous to those of methods A, B or C but using a halobenzene rather than a biphenyl as starting material. When desired, the materials in which X is halo can be converted to those in which X is metal by reactions well known to those skilled in the art such as treatment of a bromo intermediate with hexamethylditin and palladium tetrakistriphenylphosphine in toluene at reflux to yield the trimethyltin intermediate. The starting materials XXIII (B=heteroaryl) are most conveniently prepared by method C but using readily available heteroaryl rather than biphenyl starting materials. The intermediates XXII are either commercial or easily prepared from commercial materials by methods well known to those skilled in the art.

These general methods are useful for the preparation of key intermediates for which Friedel-Crafts reactions such as those of Methods A, B, C, D or E would lead to mixtures with various biaryl acylation patterns. Method F is also especially useful for the preparation of key intermediates in which the aryl groups A or B contain one or more heteroatoms (heteroaryls) such as those compounds that contain thiophene, furan, pyridine, pyrrole, oxazole, thiazole, pyrimidine or pyrazine rings or the like instead of phenyls.

Method F

$(T)_xA$-Met + X-B-E-G $\xrightarrow{Pd/(com)}$ $(T)_xA$-B-D-E-G
XXII     XXIII     I-F T, x, A, B, E and G as in Structure I
Met=Metal and X =Halide or Triflate or
Met=Halide or Triflate and X =Metal

General Method G

When the $R^6$ groups of method F form together a 4–7 member carbocyclic ring as in Intermediate XXV below, the double bond can be moved out of conjugation with the ketone group by treatment with two equivalents of a strong base such as lithium diisopropylamide or lithium hexamethylsilylamide or the like followed by acid quench to yield compounds with the structure XXVI. Reaction of XXVI with mercapto derivatives using methods analogous to those of General Method D then leads to key intermediate I-G-1 or I-G-2.

Method G

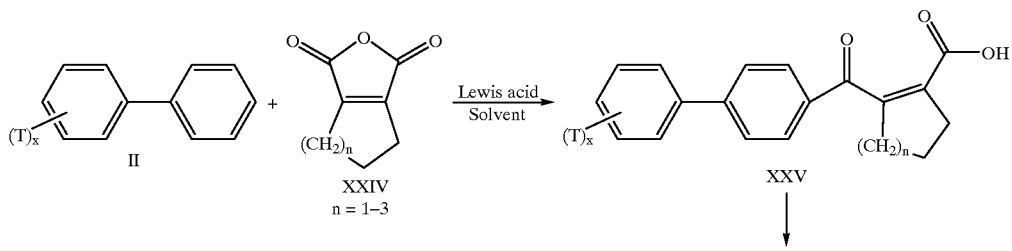

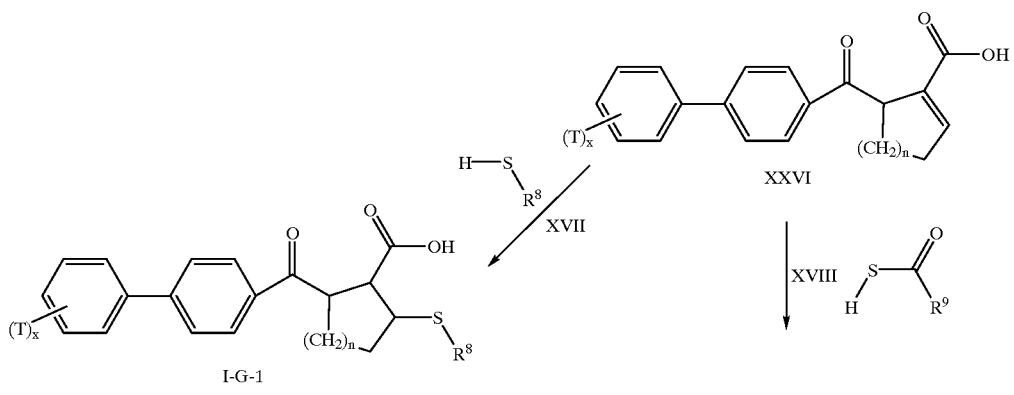

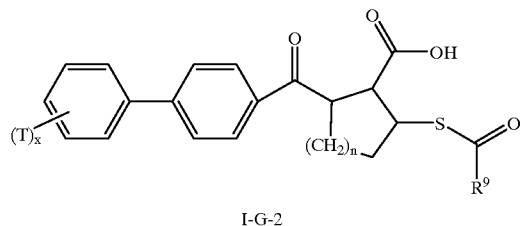

General Method H

Key intermediates in which two $R^6$ groups form a 4–7 member carbocyclic ring as in I-H below and $R^{14}$ is alkyl or arylalkyl are prepared according to method H. Starting material XXVII is reacted with two equivalents of a strong base such as lithium diisopropylamide (LDA) followed by an alkyl or arylalkyl halide ($R^{14}X$) to yield intermediate XXVIII. This material is then reduced to the alcohol with a reducing agent capable of selective reduction of the ketone such as sodium borohydride, followed by dehydration with triphenylphosphine/diethyl azodicarboxylate (DEAD) in a suitable solvent such as THF at reflux to yield XXIX. Hydrolysis of the ester with aqueous base followed by amide formation with $R^{12}ONHR^{12}$ (R is lower alkyl, but usually $CH_3$) in the presence of a coupling agent such as dicyclohexyldiimide (DCC) yields XXX. Other acyl activating groups well known to those skilled in the art such as acid chlorides or mixed anhydrides could be used instead of XXX. Substituted biphenyl halide XXXI is reacted with an alkyl lithium such as two equivalents of t-butyl lithium to yield lithiated biphenyl XXXII which is then reacted with activated acyl compound XXX. The resultant intermediate XXXIII is then treated with diethylaluminum cyanide to yield intermediate XXXIV which is then hydrolyzed with aqueous acid to yield key intermediate I-H which is purified by chromatography on silica gel to afford pure isomers.

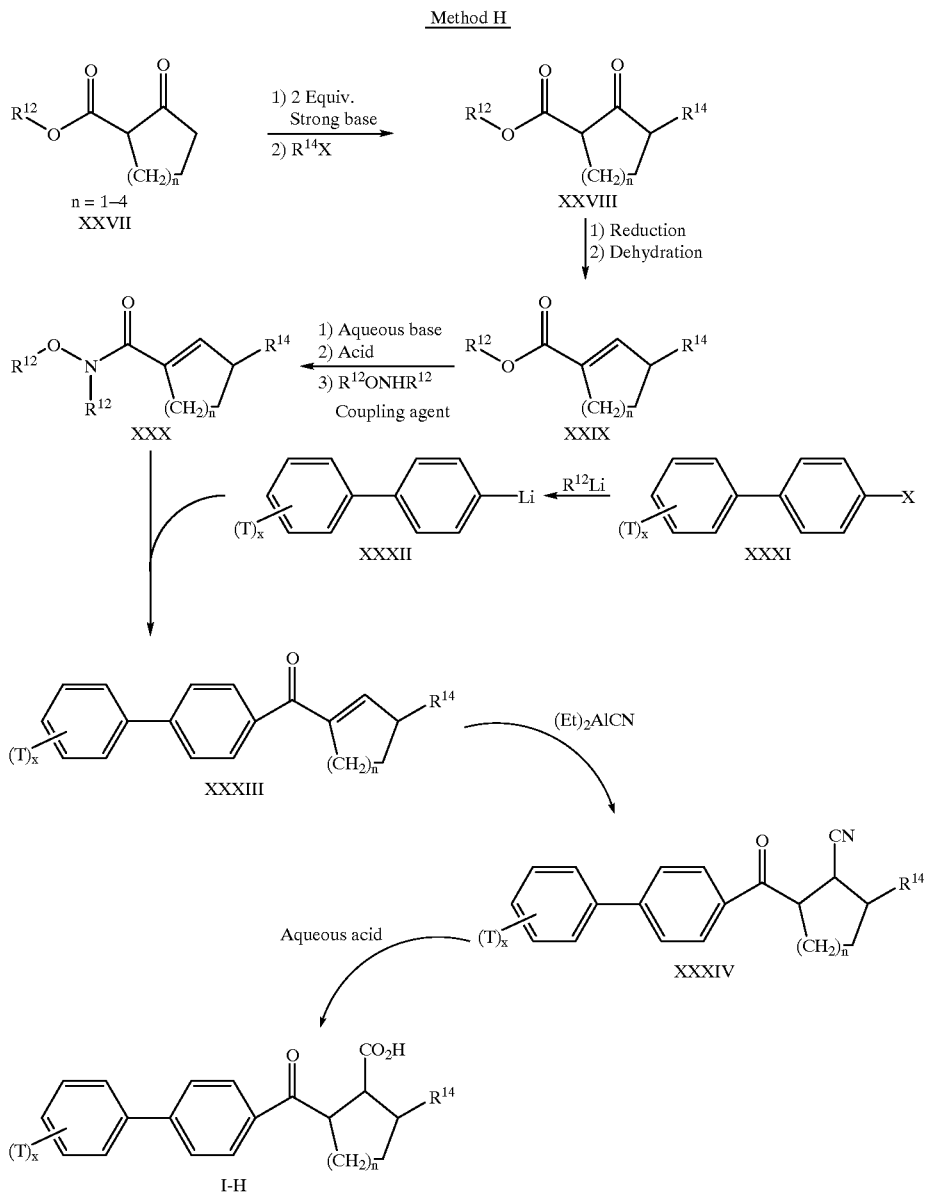

Method H

General Method I

Key intermediates in which two R6 groups together form a pyrrolidine ring are prepared according to method I. Starting material XXXV (L-pyroglutaminol) is reacted under acid catalysis with benzaldehyde XXXVI (may be substituted) to yield bicyclic derivative XXXVII. A double bond is then introduced using phenylselenenyl methodology well known to those skilled in the art to yield XXXVIII, which, in turn, is reacted with a vinylcopper (I) complex to yield conjugate addition product XXXIX. Such reactions in which Lig can be, for example, another equivalent of vinyl group or halide are well known to those skilled in the art. Hydride reduction (lithium aluminum hydride or the like) of XXXIX followed by standard blocking with, for example, t-butyldimethylsilylchloride yields XXXX which in turn is reacted with an optionally substituted benzylchloroformate XXXXI to yield XXXXII. Ozonolysis of this intermediate followed by reductive workup (dimethylsulfide, zinc/acetic acid or the like) leads to aldehyde XXXXIII. Reaction of this aldehyde with a biphenyl organometallic such as XXXII yields alcohol XXXXIV. Deblocking of the silyl group with, for example, tetrabutylammonium fluoride followed by oxidation with, for example, pyridiniumdichromate or the like yields key intermediate 1-I-1 in which $R^{14}$ is a carbobenzyloxy group.

Alternatively the carbobenzyloxy group is removed by reaction with hydrogen and a catalyst such as palladium on carbon to yield the unsubstituted key intermediate 1-I-2 optionally followed by N-alkylation to yield key intermediate 1-I-3. These final steps are well known to those skilled in the art. Alternatively the intermediate XXXX can be directly treated with ozone followed by the other steps of this method to yield 1-I-3 in which $R^{14}$ is optionally substituted benzyl rather than as in 1-I-1.

This method is especially useful to prepare single enantiomers because starting material XXXV is available as either the isomer as drawn or as D-pyroglutaminol to yield enantiomeric products.

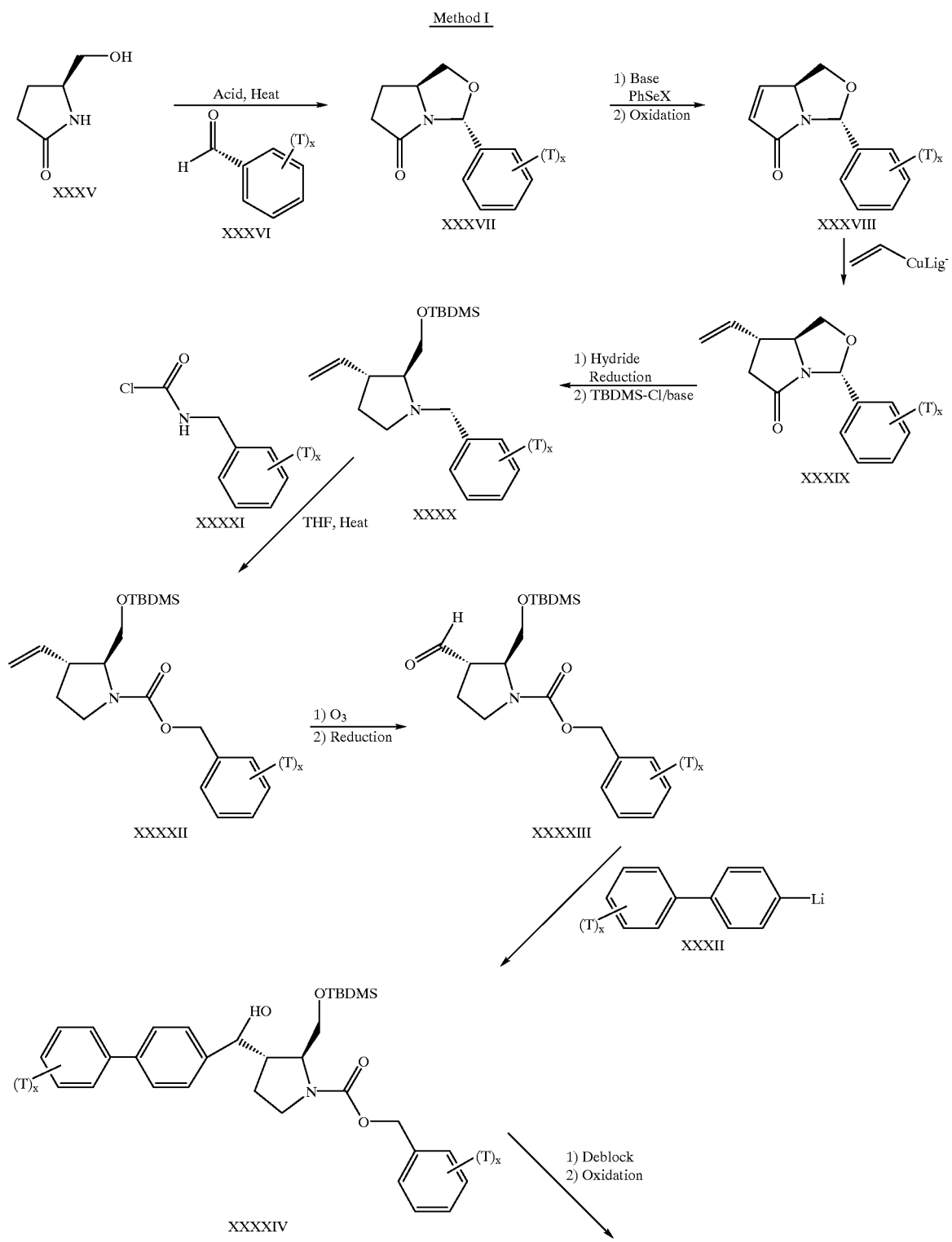

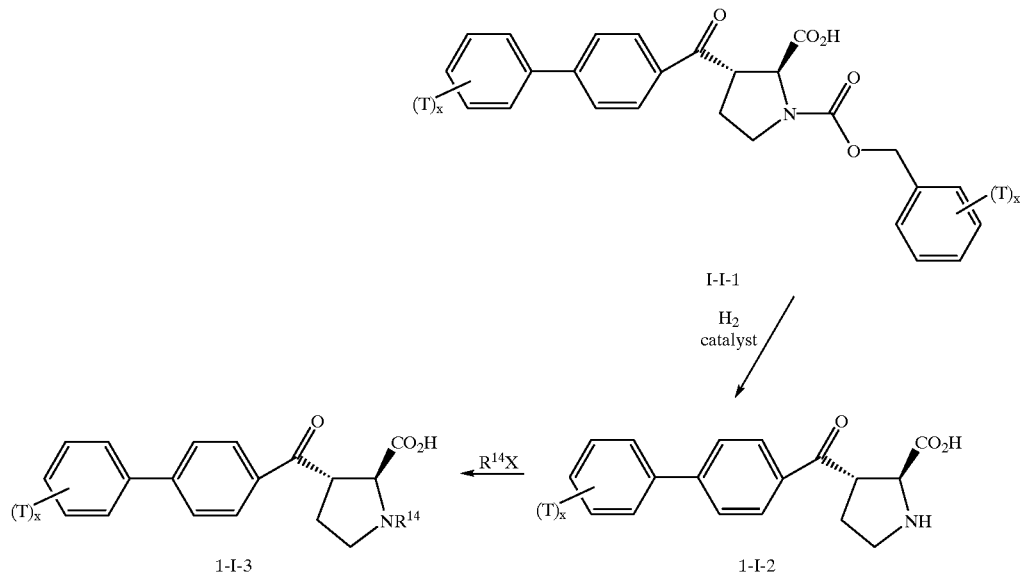

I-I-1

H₂ catalyst

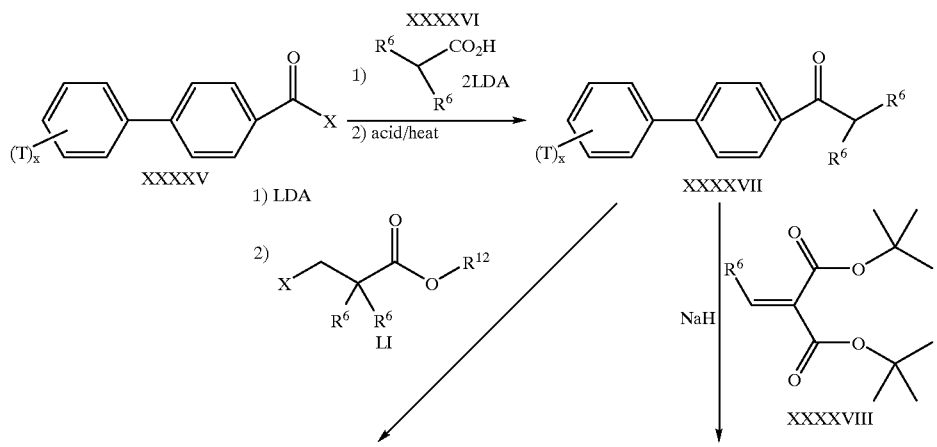

General Method J

The key intermediates in which E represents a substituted chain of 3 carbons are prepared by method J. Intermediates XXXXVII, if not available from commercial sources, are prepared by reaction of an activated biphenylcarboxylic acid derivative XXXXV with substituted acetic acid XXXXVI which has been converted to its bis anion with two equivalents of a strong base such as LDA followed by heating to decarboxylate the intermediate keto acid. Product XXXX-VII is then treated with methylenemalonate derivative XXXXVIII in the presence of a strong base such as sodium hydride to yield substituted malonate XXXXIX. This malonate can be further alkylated under conditions familiar to those skilled in the art to yield L which in turn is treated with acid and then heated to yield key intermediate 1-J-1. Alternatively the final alkylation can be omitted to yield products in which the $R^6$ adjacent to the carboxyl is H. Alternatively XXXXVII can be alkylated with 3-halopropionate ester LI in the presence of base such as LDA to yield ester 1-J-2 which can then be hydrolyzed with aqueous base to yield key intermediate 1-J-3 upon treatment with acid. This method is especially useful if any of the groups $R^6$ contain aromatic residues.

Method J

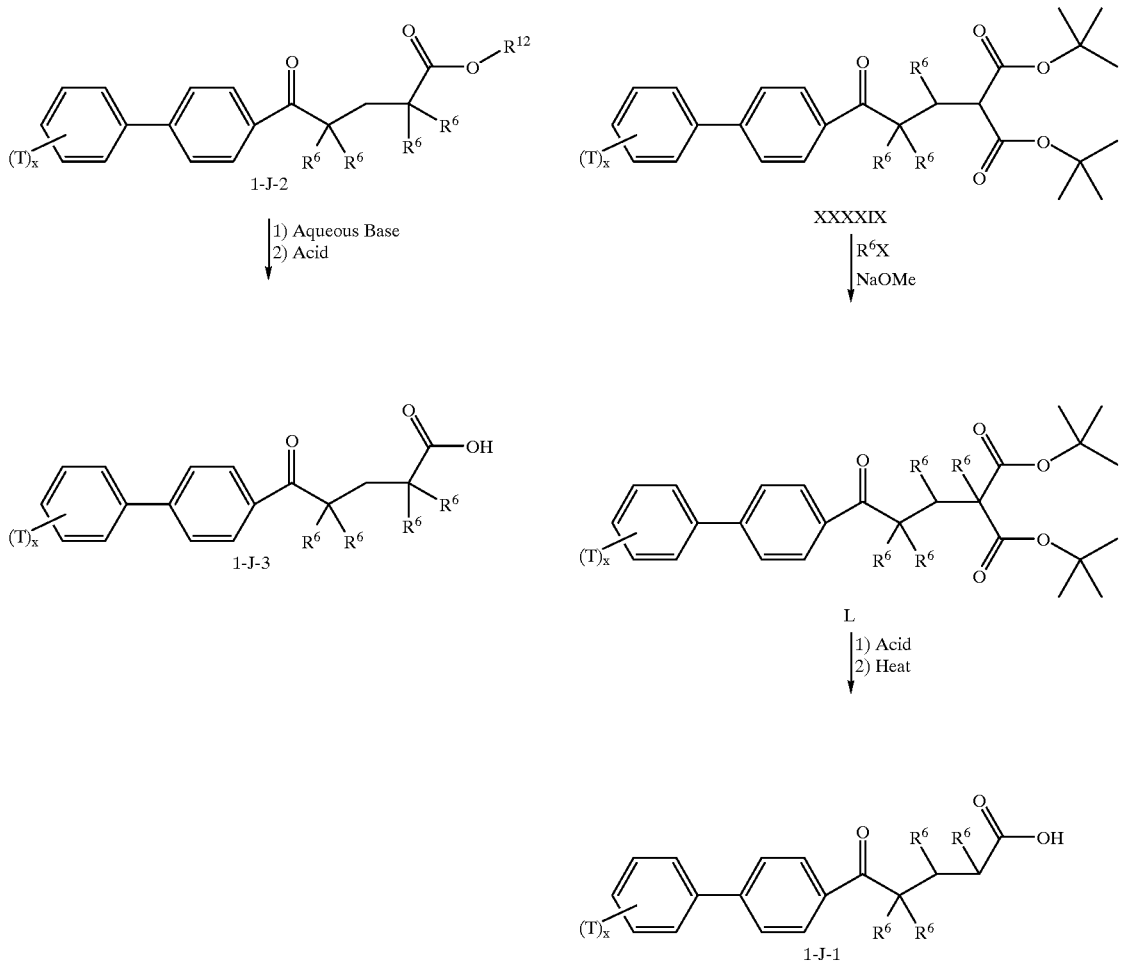

General Method K

The key intermediates in which two $R^6$ groups are joined to form a substituted 5-member ring are most conveniently prepared by method K. In this method acid LII (R=H) is prepared using the protocols described in *Tetrahedwon, Vol. 37, Suppl.*, 1981, 411. The acid is protected as an ester (R=benzyl or 2-(trimethylsilyl)ethyl) by use of coupling agents such as 1-(3-dimethylaminopropyl)-3-ethylcarbodiimide hydrochloride and procedures well known to those skilled in the art. Substituted bromobiphenyl LIII is converted to its Grignard reagent by treatment with magnesium which is then reacted with LII to yield alcohol LIV. Alcohol LIV is eliminated via base treatment of its mesylate by using conditions well known to those skilled in the art to yield olefin LV. Alternatively LIII is converted to a trimethyltin intermediate via initial metallation of the bromide with n-butyllithium at low temperature (−78°) followed by treatment with chlorotrimethyltin and LII is converted to an enoltriflate by reaction with 2-[N,N-bis(trifluoromethylsulfonyl)amino]-5-chloropyridine in the presence of a strong aprotic base. The tin and enoltriflate intermediates are then coupled in the presence of a Pd° catalyst, CuI and $AsPh_3$ to yield directly intermediate LV. Ozonolysis of LV (workup with methyl sulfide) yields aldehyde LVI. Alternatively treatment with $OsO_4$ followed by $HIO_4$ converts LV to LVI.

Conversion of intermediate LVI to key intermediate I-K is accomplished in several ways depending on the identity of side chain function X. Reaction of LVI with Wittig reagents followed by hydrogenation yields products in which X is alkyl, aryl or arylalkyl. Reduction of aldehyde LVI with LAH yields alcohol I-K (X=OH). The alcohol is converted to phenyl ethers or N-phthalimidoyl compounds by use of the appropriate starting materials and Mitsunobu conditions well known to those skilled in the art; see O Mitsunobu, *Synthesis*, 1 (1981). Alternatively the alcohol of I-K (X=OH) is converted to a leaving group such as tosylate (X=OTs) or bromide (X=Br) by conditions well known to those skilled in the art and then the leaving group is displaced by sulfur or azide nucleophiles to yield products with X=thioether or azide which in turn is reduced and acylated to yield amides (X=NHAcyl). Direct acylation of the alcohol I-K (X=OH) yields key intermediates in which X=OAcyl and reaction of the alcohol with various alkyl halides in the presence of base yields alkyl ethers (X=$OR^2$). In each case a final step is removal of acid blocking group R to yield acids (R=H) by using conditions which depend on the stability of R and X, but in all cases well known to those skilled in the art such as removal of benzyl by base hydrolysis or of 2-(trimethylsilyl)ethyl by treatment with tetrabutylammonium fluoride.

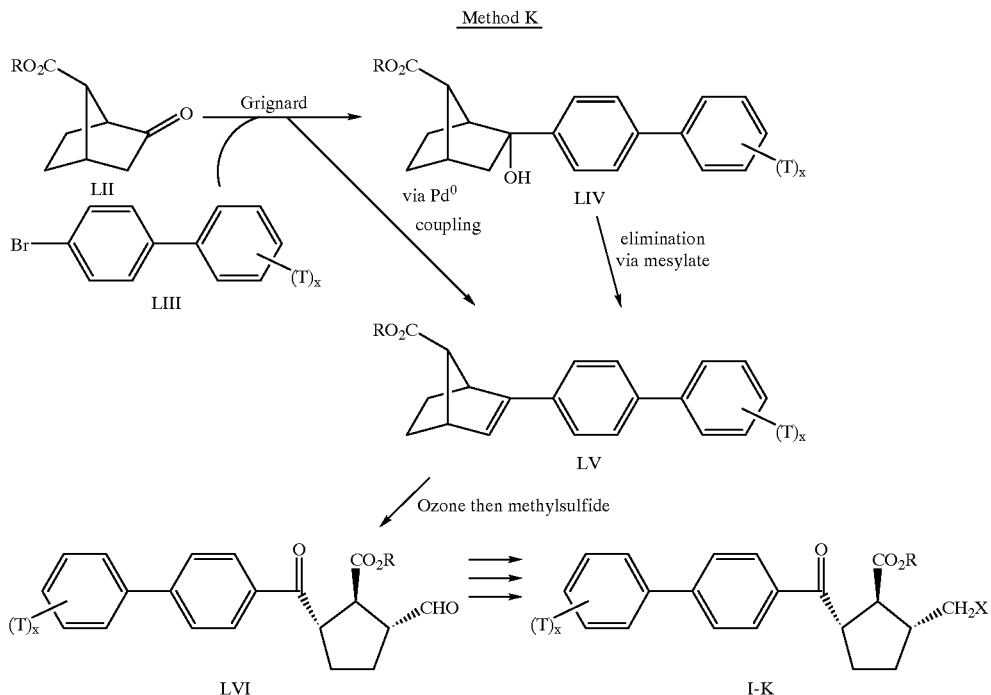

Method K

Method L

The 4-oxobutanoic or 5-oxopentanoic acids LVII which have been prepared by one of methods A through K are reduced to hydroxyacids LVIII by the action of a selective hydride reducing agent such as sodium borohydride, sodium triacetoxyborohydride, or sodium cyanoborohydride in a suitable solvent such as water, ethanol or tetrahydrofuran at 0° C. to ambient temperature. Alternatively, the reducing agent can be any number of other reagents used by one skilled in the art to reduce a carbonyl to a secondary alcohol, with the proviso that such reducing agent does not effect undesired changes in the T, carboxy, or $R^6$ moieties of the oxoacids. The isomers of the product can be isolated in pure form by a combination of crystallization and chromatography.

Hydroxyacid LVIII is converted to lactone LIX by reaction with a catalytic amount of acid such as toluenesulfonic acid or camphorsulfonic acid in a suitable solvent such as benzene, toluene or methylene chloride at between 0° C. and reflux.

Reaction of lactone LIX with hydroxylamine derivation $NH_2OR^{11}$ in a suitable solvent such as ethanol, methanol, THF, toluene, or methylene chloride in the presence of a suitable catalyst such as sodium hydroxide, sodium methoxide, triethylamine, N-ethylmorpholine, trimethylaluminum, or dimethylaluminum chloride leads to intermediate LX. $R^{11}$ may be H, in which case LX is an invention compound, or $R^{11}$ may be a blocking group such as benzyl, trimethylsilyl, or tert-butyldimethylsilyl. If $R^{11}$ is a blocking group, then it is removed by a suitable reaction such as hydrogenation or transfer hydrogenation when $R^{11}$ is benzyl or treatment with $(n-Bu)_4NF$ or acid when $R^{11}$ is trialkylsilyl to yield invention compound I-L. The choice of catalyst and blocking group $R^{11}$ is dictated by the proviso that the conditions used do not effect undesired changes in the T or $R^6$ moieties of the invention compounds. For example, when $R^6$ contains a phthalimide moiety which is sensitive to base, acid conditions are chosen by one skilled in the art.

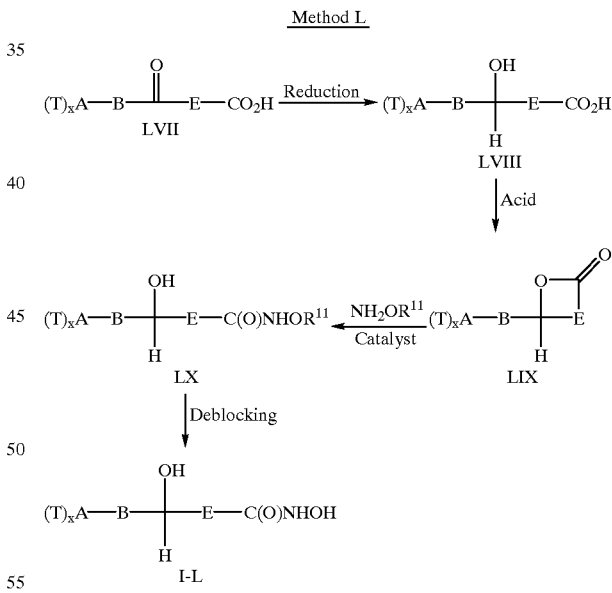

Method L

Method M

Alternatively, the 4- or 5-hydroxyhydroxamic acids may be prepared as shown in Method M. The hydroxy acid LVIII is converted to the O-tert-butyldimethylsilyloxy acid LXII as shown according to the methods described by D. J. Abraham, et al., J. Med. Chem., 27, 1549–1559 (1984). Intermediate LXII can be converted to the activated ester LXII in which X is, for example, iso-butoxycarbonyloxy by reaction with isobutyl chloroformate in an a suitable solvent in the presence of a suitable tertiary amine base such as triethylamine. Reaction of intermediate LXIII with a hydroxylamine derivative such as O-tert-butyldimethylsilyl hydroxylamine yields intermediate LXIV. Alternatively, LXII may be converted directly to LXIV by treatment with a mixture of O-tert-butyldimethylsilyl hydroxylamine and a suitable coupling agent such as 1-(3-dimethylaminopropyl)-3-ethylcarbodiimide methiodide in a suitable solvent such as THF or methylene chloride. Intermediate LXIV is then converted to invention compound I-L by treatment with reagents such as acetic acid/water mixtures, aqueous mineral acid or (n-butyl)$_4$NF. The choice of deblocking conditions is dictated by the proviso that the conditions used do not effect undesired changes in the T or $R^6$ moieties of the invention compounds.

-continued

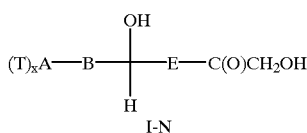

I-N

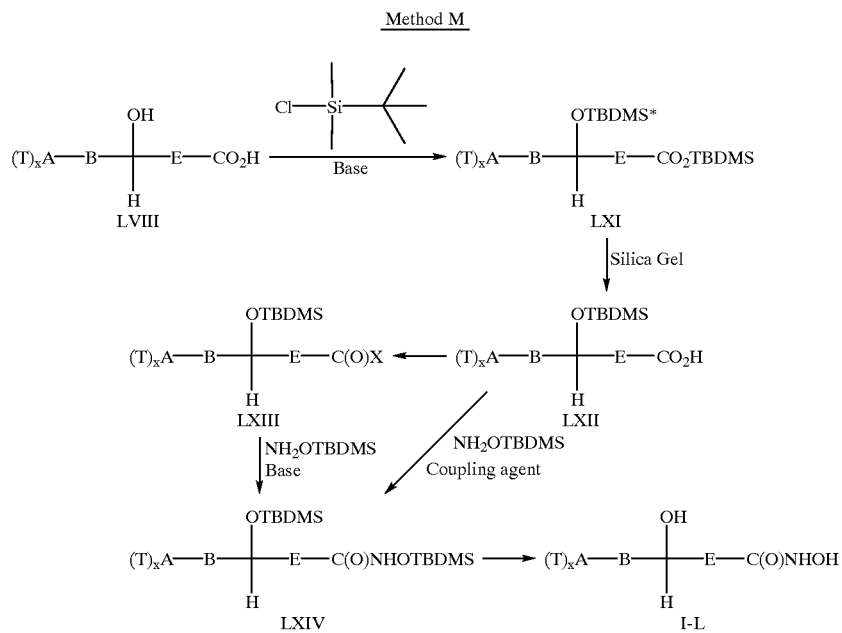

Method M

*TBDMS = tert-butyldimethylsilyl

Method N

The 1-hydroxymethylketone pro drugs of the invention are prepared as shown in method N. Thus the active acyl intermediate LXIII is reacted with diazomethane to yield diazomethylketone LXIV which in turn is treated with aqueous sulfuric acid to both convert the diazo group to a hydroxyl and remove the TBDMS group to yield invention compound I-N. Alternatively, LXIII can be treated with 1,1,2-tris-(trimethylsilyloxy)ethylene in the presence of SnCl$_4$, followed by aqueous acid to yield I-N.

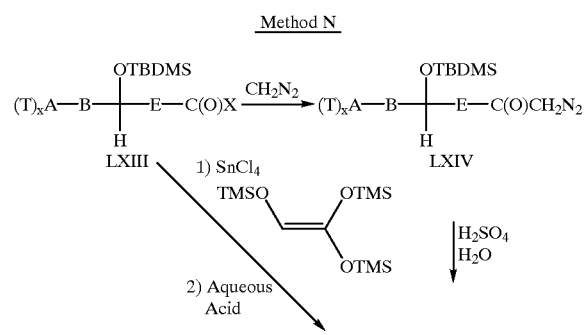

Method N

Method O

Invention compounds in which D is a carbonyl are most conveniently prepared as shown in Method O. Intermediate I-C-6 from Method C-2 is first converted to the active acyl compound LXV by methods well known to those skilled in the art. Intermediate LXV may be an acid halide or mixed anhydride. Reaction of LXV with diazomethane yields diazomethyl ketone LXVI which, in turn, is converted to invention compound I-O-1 by treatment with aqueous sulfuric acid. Intermediate LXV may also be converted to hydroxamic acid derivative LXVII by treatment with hydroxylamine derivative NH$_2$OR$^{11}$, in which $R^{11}$ may be H, tert-butyl or trialkylsilyl. Intermediate LXVII is then converted to invention compound I-O-2 by treatment with aqueous acid. Condensation of I-O-1 with one equivalent of NH$_2$Y$^2$ in a suitable solvent in the presence of a suitable catalyst well known to those skilled in the art yields a mixture of oximes, oxime ethers or hydrazones from which invention compound I-O-3 can be isolated by chromatography. In this step, $Y^2$ is defined as OR$^2$ or N(R$^2$)$_2$ in which the $R^2$ groups can be the same or different. Condensation of I-O-2 with NH$_2$Y$^2$ in a similar way leads to invention compound I-O-4.

Method O

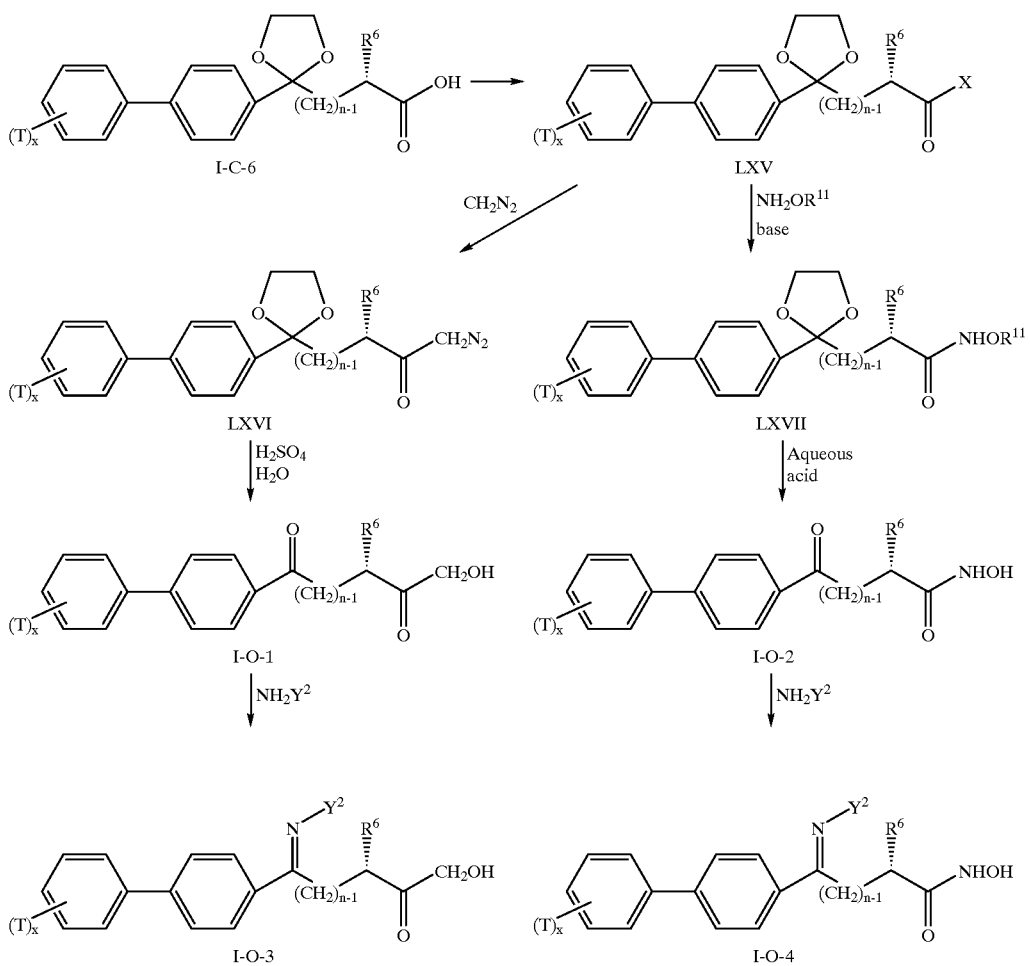

Method P

Invention compounds with an acylsulfonamide as carboxy isostere are prepared according to Method P. Intermediate LVII is first activated by conversion to an acid halide or preferentially to a mixed anhydride using methods well known to those skilled in the art and then the activated intermediate is reacted with $NH_2S(O)_2R^3$ to yield invention compound I-P-1. Alternatively, a coupling agent such as 1,1'-carbonyldiimidazole and a base such as DBU can be used together with $NH_2S(O)_2R^3$ to effect this transformation Reduction of the keto moiety of I-P-1 is conducted by use of a mild reducing agent such as sodium borohydride in a suitable solvent such as ethanol to yield invention compound I-P-2. Alternatively, Intermediate LXIII is reacted with $NH_2S(O)_2R^3$ in the presence of a suitable base and the resultant intermediate is treated with acid or tetrabutylammonium fluoride to yield invention compound I-P-2. Condensation of I-P-1 with $NH_2Y^2$ yields invention compound I-P-3.

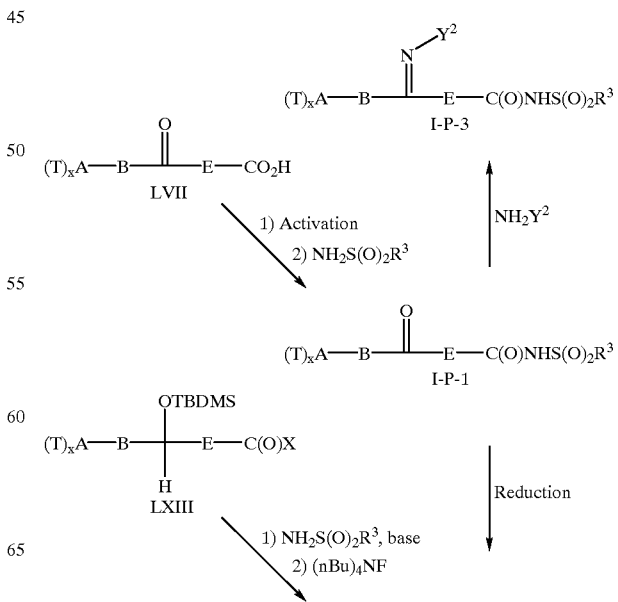

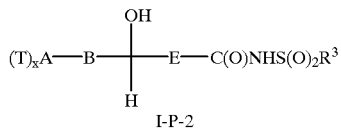

I-P-2

Suitable pharmaceutically acceptable salts of the compounds of the present invention that contain an acidic moiety include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

Suitable pharmaceutically acceptable salts of the compounds of the present invention that contain a basic moiety include addition salts formed with organic or inorganic acids. The salt forming ion derived from such acids can be halide ions or ions of natural or unnatural carboxylic or sulfonic acids, of which a number are known for this purpose. Examples include chlorides, acetates, tartrates, or salts derived from amino acids like glycine or the like. The physiologically acceptable salts such as the chloride salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine or either isomer of α-methylbenzyl amine or pure acids such as either isomer of tartaric acid in suitable solvents can yield salt crystals of a single enantiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the invention compound with an equivalent of the base supplying the desired basic ion or the basic form of the invention compound with an equivalent of the acid supplying the desired acid ion in a medium in which the salt precipitates or in aqueous medium and then lyophilizing. The free acid or basic form of the invention compounds can be obtained from the salt by conventional neutralization techniques, e.g., with potassium bisulfate, hydrochloric acid, sodium hydroxide, sodium bicarbonate, etc.

The compounds of the present invention are expected to inhibit the matrix metalloproteases MMP-1, MMP-2, MMP-3, MMP-8, MMP-9, MMP-12, MMP-13, and the related protease TACE, as well as the release of TNFα in vivo, and are therefore expected to be useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the $R^6$ groups of the claimed compounds, is expected to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated or TNFα release-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 μm) such as those comprising cellulose, polyacrylate or polycarbophil, in conjunction with suitable absorption enhancers such as phospholipids or acylcarnitines. Available systems include those developed by DanBiosys and Scios Nova.

Oral delivery may be achieved by incorporation of the drug into tablets, coated tablets, dragées, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition. It is expected that the compounds of the invention generally will be administered in doses in the range of 0.01–100 mg per kg of body weight per day.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

EXPERIMENTAL

General Procedures

All reactions were performed in flame-dried or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated. The disclosure of published application WO 09615096 is hereby incorporated by reference.

Materials

Commercial grade reagents and solvents were used without further purification except that diethyl ether and tetrahydrofuran were usually distilled under argon from benzophenone ketyl, and methylene chloride was distilled under argon from calcium hydride. A number of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography

Analytical thin-layer chromatography (TLC) was performed on Whatman® pre-coated glass-backed silica gel 60 A F-254 250 μm plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semi-preparative HPLC was performed at 24 mL min$^{-1}$ on a 21.4×250 mm Microsorb® column monitored at 288 nm.

Instrumentation

Proton ($^1$H) nuclear magnetic resonance (NMR) spectra were measured with a General Electric GN-OMEGA 300 (300 MHz) spectrometer, and carbon thirteen ($^{13}$C) NMR spectra were measured with a General Electric GN-OMEGA 300 (75 MHz) spectrometer. Most of the compounds synthesized in the experiments below were analyzed by nmr, and the spectra were consistent with the proposed structures in each case.

Mass spectral (MS) data were obtained on a Kratos Concept 1-H spectrometer by liquid-cesium secondary ion (LCIMS), an updated version of fast atom bombardment (FAB). Most of the compounds synthesized in the experiments below were analyzed by mass spectroscopy, and the spectra were consistent with the proposed structures in each case.

General Comments

For multi-step procedures, sequential steps are noted by numbers. Variations within steps are noted by letters. Dashed lines in tabular data indicates point of attachment.

EXAMPLE 1

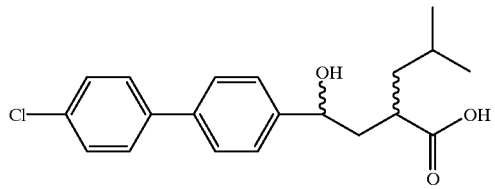

Step 1

4-[4-(4-Chlorophenyl)phenyl]-4-oxo-2-isobutylbutanoic acid was prepared as described in WO-09615096 (Example 1). A portion of this material (103.5 mg, 0.300 mmol) was dissolved in 20 ml of water with the addition of 30.0 mg (0.687 mmol) of sodium hydroxide. The solution was cooled in an ice bath and then 13.0 mg (0.344 mmoles) of sodium borohydride was added as a solid. Stirring continued for 1 h. TLC (methylene chloride-2.5% methanol) indicated that starting material was still present, so the reaction was allowed to warm to room temperature overnight (16.5 h). Starting material was still present, so 13.0 mg more sodium borohydride was added at room temperature. The reaction was stirred for 2 h and then quenched with 10% HCl and extracted twice with ethyl acetate. The combined organic extracts were washed once with brine and dried over MgSO$_4$. The solution was concentrated in vacuo to give 57.0 mg of a crude solid. This was purified by silica gel chromatography (methylene chloride-methanol) to give two major 4-hydroxybutyric acid products A (7.9 mg) and B (19.1 mg).

Compound A: $^1$H NMR (MeOD-d$_3$) δ7.56 (m, 4H), 7.38 (m, 4H), 4.66 (dd, J=9 Hz, J=3 Hz, 1H), 2.77 (m, 1H),1.95 (m, 1H), 1.75, 1.57 (m, 3H), 1.26 (m, 1H), 0.85 (d, J=6 Hz, 3H), 0.79 (d, J=6 Hz, 3H).

Compound B: $^1$H NMR (MeOD-d$_3$) δ7.58 (m, 4H), 7.40 (m, 4H), 4.64 (t, J=6 Hz, 1H), 2.34 (m, 1H), 2.10 (m and solvent), 1.74 (m, 1H), 1.54 (m, 2H), 1.28 (m, 2H), 0.87 (d, J=6 Hz, 3H), 0.77 (d, J=6 Hz, 3H).

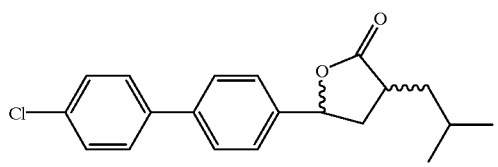

Step 2

The lactones C and D were prepared by dissolving a mixture of hydroxyacids A and B (51 mg) in 25 ml benzene along with camphor sulfonic acid (11 mg). This mixture was refluxed for 12 hours using a Dean-Stark trap. The resultant solution was washed with aqueous sodium bicarbonate, dried over $MgSO_4$ and evaporated in vacuo. The residue was purified by silica gel chromatography with Hexane-EtOAc to give the separated lactones.

Lactone C: $^1$H NMR ($CDCl_3$) δ7.3–7.7 (m, 8H), 5.6 (m, 1H), 2.75 (m, 1H), 2.45 (m, 2H), 2.20 (solvent), 1.75 (m, 2H), 1.45 (m, 1H), 1.01 (d, J=7 Hz, 3H), 0.87 (d, J=7 Hz, 3H); MS (FAB-LSIMS) 329 $[M+H]^+$ ($C_{20}H_{21}O_2Cl$ FW=328.87).

Lactone D: $^1$H NMR ($CDCl_3$) δ (m, 8H), (m, 1H), (m, 1H), 2 (m, 2H), 2.20 (solvent), 1.75 (m, 2H), 1.45 (m, 1H), 1.01 (d, J=7 Hz, 3H), 0.87 (d, J=7 Hz, 3H); MS (FAB-LSIMS) 328 $[M]^+$ ($C_{20}H_{21}O_2Cl$ FW=328.87).

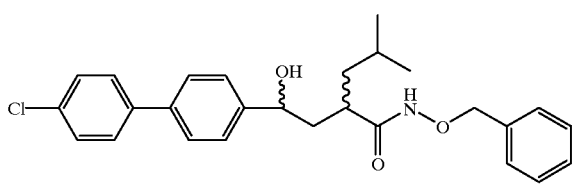

Step 3

O-Benzylhydroxylamine hydrochloride (22.3 mg, 0.14 mmol) was suspended in dry acetonitrile (1 ml) with ice/salt bath cooling as a solution of trimethylaluminum in toluene (0.07 ml, 2 M, 0.14 mmol) was added. After stirring for 1 hr at cold temperature, the mixture was allowed to come to room temperature for 2.5 hr. before a solution of C and D lactone mixture from step 2 (22 mg in 0.5 ml) was added. After stirring for two hours the product could be seen to form by tlc analysis. Lactone mixture $R_f$ 0.86, product isomers $R_f$ 0.15 and 0.19 (2.5% methanol in methylene chloride). After stirring overnight the product mixture was quenched by mixing with aqueous hydrochloric acid and extracted with ethyl acetate. The desired products along with some recovered starting materials can be isolated in pure form from the extract by chromatography.

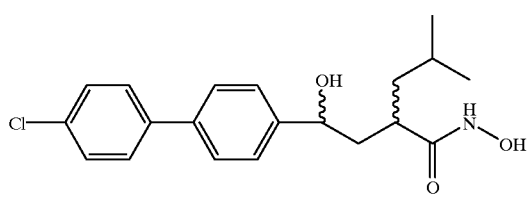

Step 4

The benzyl blocked products of step 3 can be de-blocked by hydrogenation at between atmospheric pressure and 60 PSI hydrogen gas in methanol in the presence of 5–10% palladium on carbon to yield the desired invention compound hydroxamic acids.

EXAMPLE 2

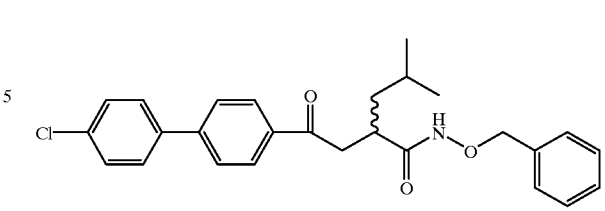

Step 1

The alcohol products of step 3 of example 1 can be dissolved in acetone and oxidized with chromic acid (Jones reagent) at between 0° C. and room temperature to yield the keto compound.

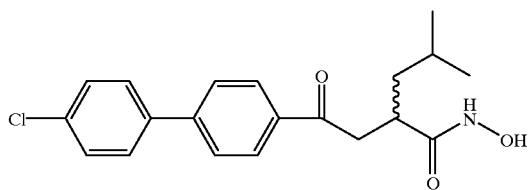

Step 2

The products of step 1 can be de-blocked by hydrogenation at between atmospheric pressure and 60 PSI hydrogen gas in methanol in the presence of 5–10% palladium on carbon to yield the desired invention compound hydroxamic acids.

EXAMPLE 3

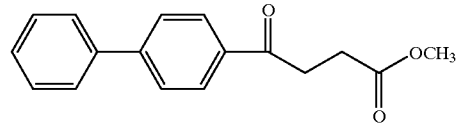

Step 1

A solution of 4-oxo-4-biphenylbutyric acid (500 mg) in ethyl acetate (50 ml)/methylene chloride (5 ml) was stirred with ice bath cooling as an etherial solution of diazomethane was added slowly until the yellow color of excess reagent persisted. The resultant solution was evaporated in vacuo to yield pure methyl ester (528 mg, 100%).

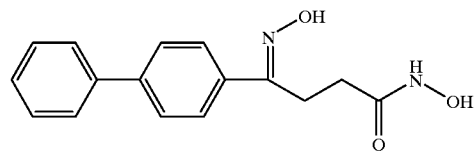

Step 2

A solution of hydroxylamine hydrochloride (110 mg, 1.58 mmol) in methanol (2 ml) was prepared by warming and then a second solution of potassium hydroxide (183 mg, 3.26 mmol) in water (1 ml) was added. The resultant mixture was cooled in an ice bath and stirred as the product from step 1 above (200 mg, 0.74 mmol) was added. The resultant mixture was warmed and sonicated to form a homogeneous solution before it was re-cooled and partially evaporated to remove methanol. A 10% aqueous acetic acid solution (ca. 20 ml) was added. A white precipitate of the invention compound (133 mg) formed which was collected by filtration and dried in vacuo.

EXAMPLE 4

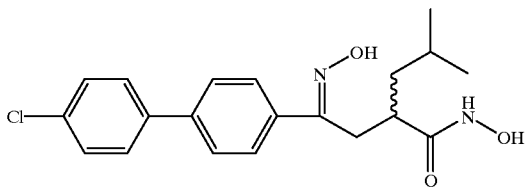

A mixture of the product Example 2 (1 mmol), hydroxylamine hydrochloride (1.1 mmol), and sodium carbonate (1.1 mmol) in dry ethanol can be refluxed under argon to form the invention compound. After cooling, the product can be recovered by evaporation to remove solvents and then mixed with 10% acetic acid and processed as in example 3 to yield purified material.

EXAMPLE 5

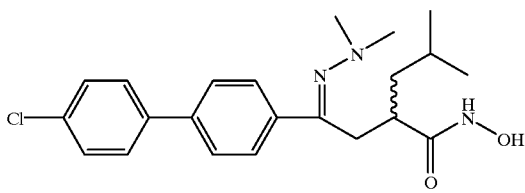

A mixture of the product of Example 2 (1 mmol) and 1,1-dimethylhydrazine (2.2 mmol) in absolute ethanol (4 ml) can be refluxed under argon to yield the invention compound. The product solution can be evaporated in vacuo and the residue chromatographed to yield pure material.

EXAMPLES 6 AND 7

Compound F

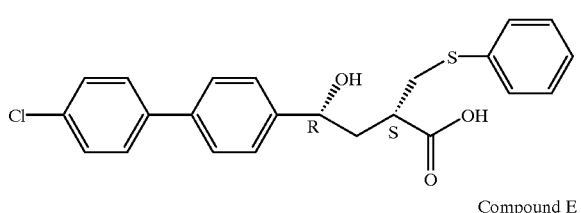

Compound E

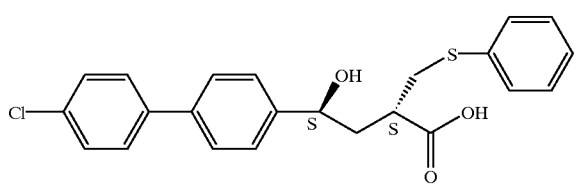

Compound G

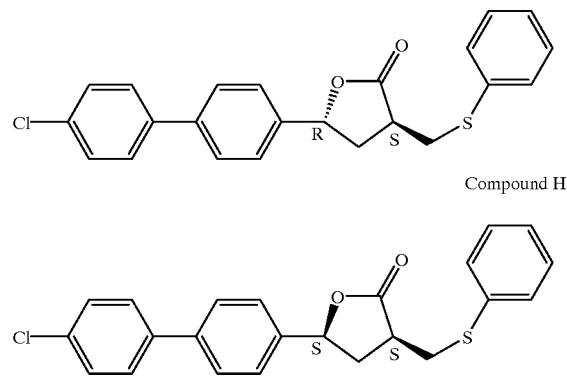

Compound H

Step 1

[S]-4-[4-(4-Chlorophenyl)phenyl]-4-oxo-2-(phenylthiomethyl)-butanoic acid was prepared as described in WO-09615096 (Example 197). A solution of this material (6.52 g, 15.9 mmol) in absolute ethanol (100 ml) was stirred under argon with ice bath (0° C.) cooling as sodium borohydride (4.12 g, 109 mmol) was added in portions. The reaction mixture was stirred as the ice bath melted and then at ambient temperature overnight. The resultant mixture which contained significant white solid was quenched by the addition of water (100 ml) and then evaporated in vacuo to ca. ⅓ volume. The condensed mixture was mixed with ca. 100 ml of ethyl acetate and then mixed vigorously as it was cautiously quenched with 1N hydrochloric acid until the aqueous phase was strongly acidic (evolution of hydrogen gas from excess borohydride). The aqueous phase was removed and the organic was washed several times with water, then brine and then dried over sodium sulfate and evaporated in vacuo. The residue was dissolved as much as possible in 100 ml of a methylene chloride/methanol mixture (99:1) and then filtered to remove a white solid which proved to be pure single isomer E ([2S,4S]-4-[4-(4-chlorophenyl)phenyl]-4-hydroxy-2-(phenylthiomethyl)-butanoic acid) as shown by analytical HPLC (silica column, 1 ml/min. 99:1 methylene chloride/methanol plus 0.05% acetic acid, peak detection at 254 nM, this 4-S isomer is the second to elute).

The filtrate was chromatographed on a preparative (46 mm ID) silica HPLC column using the same solvent at 80 ml/min. to yield 444 mg of pure F (4R isomer) by condensation of the best fractions in vacuo to a low volume, cooling and collection of crystals by filtration.

Preparative HPLC of the combined early fractions using either 5% ethyl acetate in hexane or a slow gradient of 0–1% methanol in methylene chloride led to the isolation of pure samples of each of the γ-butyrolactone isomers (G and H).

Determination of the relative stereochemistry around chiral ring carbons can be achieved by identifying the relative position of the protons attached to these carbons, i.e. whether pairs of protons are on the same or on the opposite side of the ring plane. NMR spectroscopy, in particular one- or two-dimensional nuclear Overhauser spectroscopy (NOESY), is the ideal technique to solve this problem, taking advantage of differential nuclear Overhauser enhancements (NOEs) based on the relative spatial proximity of protons. See Macura, S. and Ernst, R. R., *J. Mol. Biol.*, 1980, 206, 397. This was done for the two isomers of the γ-butyrolactone to show a greater NOE between H-1 and H-4 of the isomer with those protons cis(2S,4S) than that of the isomer with those protons trans(2S,4R). All other NOEs observed between the other protons on the lactone ring and attached CH$_2$ of the two isomers were self consistent with this interpretation.

While the purified crystalline hydroxy acids (Compounds E and F) are relatively stable as solids, aged solutions of these compounds slowly showed one or other of the lactones as a result of spontaneous lactonization occurring. This was evidenced by the chemical shift of H-4 on the 4S lactone at δ5.40 ppm and that on the 4R lactone at δ5.65 ppm. The hydroxy acid that converted to the 2S,4R lactone was thus identified as the 2S,4R hydroxy acid (Compound E) and that which converted to the 2S,4S lactone was identified as the 2S,4S hydroxy acid (Compound F).

Compound E (2S,4R): MP 122–123° C.; HPLC (1 ml/min. 1% methanol in methylene chloride plus 0.05% acetic acid, Rainin 4.6 mm×25 cm silica column) $^rR$=10.02 min.; [α]$_D$+64.4° (c 0.55, acetone); $^1$HNMR (Acetone-d$_6$) δ7.12–7.7 (m, 13H), 4.82 (dd, J=4.04, 8.45 Hz, 1H), 3.2 (m, 2H), 2.98 (m, 1H), others under acetone peak.

Compound F (2S,4S): MP 137–138° C.; HPLC (conditions above) $^rR$=13.11 min.; [α]$_D$++28.8° (c 0.93, acetone); $^1$HNMR (Acetone-d$_6$) δ7.15–7.7 (m, 13H), 4.83 (dd, J=5.88, 8.46 Hz, 1H), 3.25 (d, J=6.61 Hz, 2H), 2.79 (m, 1H), 1.95–2.25 (m, 2H).

Compound G (2S,4R): MP 122–123° C.; $^1$HNMR (CDCl$_3$, 500 MHz) δ7.21–7.60 (series of m, 13H, aromatic H), 5.65 (dd, J=4.59, 7.98 Hz, 1H, H-4), 3.55 (dd, J=3.74, 13.29 Hz, 1H, SCH), 3.04 (dd, J=9.97, 13.28 Hz, 1H, SCH), 2.94–2.98 (m, 1H, H-2), 2.64–2.70 (m, 1H, H-3A), 2.46–2.51 (m, 1H, H-3B).

Compound H (2S,4S): MP 142–143° C.; $^1$HNMR (CDCl$_3$, 500 MHz) δ7.21–7.60 (series of m, 13H, aromatic H), 5.40 (dd, J=5.79, 10.58 Hz, 1H, H-4), 3.65 (dd, J=3.50, 13.40 Hz, 1H, SCH), 2.96 (dd, J=9.90, 13.37 Hz, 1H, SCH), 3.02–3.07 (m, 1H, H-2), 2.87–2.92 (m, 1H, H-3A), 2.07 (dd, J=12.26, 23.08 Hz, 1H, H-3B).

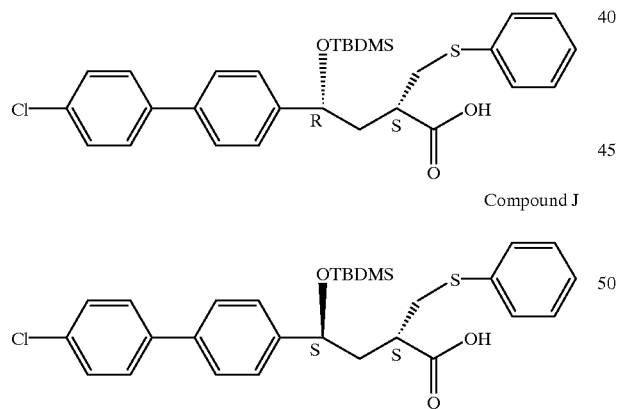

Compound I

Compound J

Step 2

This step follows the general process reported by D. J. Abraham, et al., J. Med. Chem., 27, 1549–1559 (1984). Thus the product E or F from step 1 (1 mmol) can be reacted with tert-butyldimethylsilyl chloride (3 mmol) and imidazole (7.3 mmol) in dry tetrahydrofuran (3 ml) and dry DMF (1 ml) under argon at ambient temperature for about 2 days and then the solid removed by filtration and the filtrate evaporated in vacuo to yield a residue of deblocked material. This residue can be purified by chromatography on silica gel to both deblock the acid function and purify the products I or J.

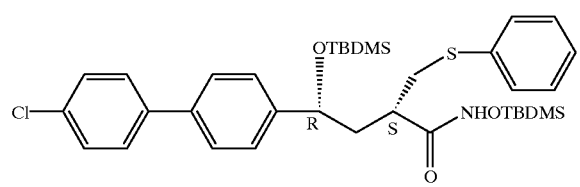

Compound K

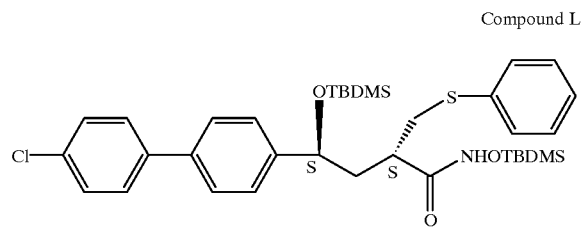

Compound L

Step 3

A dry methylene chloride solution of the product I or J from step 2 (1 mmol), O-tert-butyldimethylsilyl hyroxylamine (1–4 mmol) and 1-hydroxybenzotriazole (1 mmol) can be cooled in an ice bath as 1-ethyl-3-(3-dimethylaminopropyl)carbodiimide (1–1.5 mmol) is added. After the reaction mixture has stirred for several hours at 0° C., it is left to stir at ambient temperature until a TLC assay indicates that the starting material I or J has been substantially consumed. The product K or L can be isolated by dilution with dilute hydrochloric acid, extraction with methylene chloride, evaporation of the extracts and chromatography and/or recrystallization of the residue.

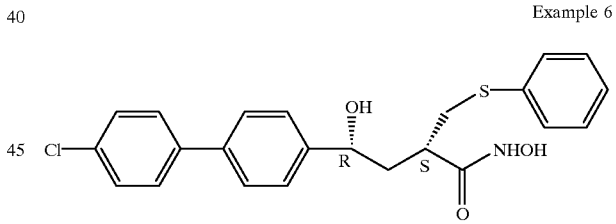

Example 6

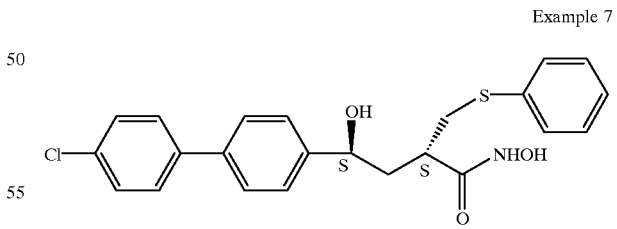

Example 7

Step 4

The blocked materials K or L can be mixed with acetic acid, water and tetrahydrofuran (3:1:1) at ambient temperature for 1–24 hr until a TLC assay indicates substantial product has formed. The resultant invention compounds 6 or 7 can be purified by chromatography.

EXAMPLE 8 AND 9

Compound M

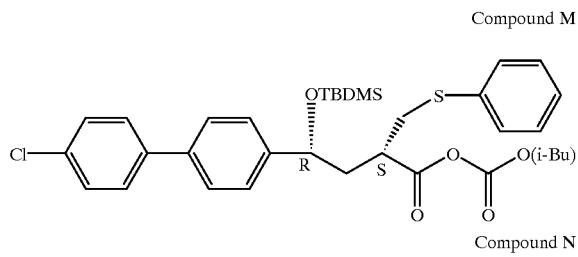

Compound N

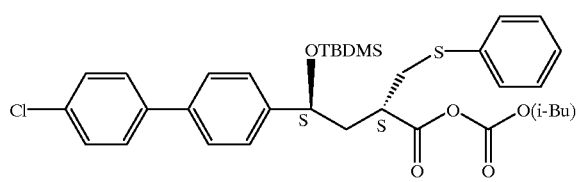

Step 1

Compound I or J from Examples 6 or 7 (1 mmol) can be reacted with isobutylchloroformate (1–1.2 mmol) and imidazole (1–2 mmol) in dry methylene chloride or tetrahydrofuran at between −78 and 0° C. to yield the mixed anhydride M or N which is used directly in solution in the next step.

Example 8

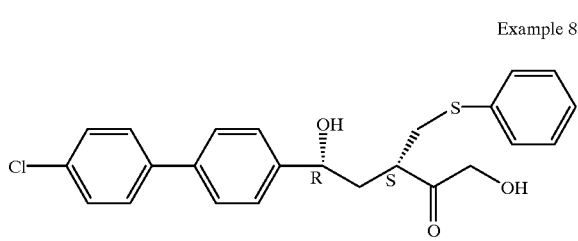

Example 9

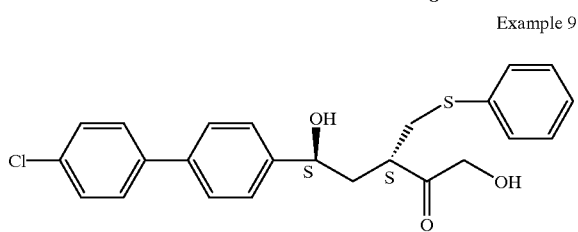

Step 2

Compounds M or N from step 1 (1 mmol) can be reacted with an ether solution of diazomethane with ice bath cooling to yield the diazomethylketone, which is then treated with aqueous sulfuric acid to give the hydroxymethyl ketone invention compound 8 or 9.

EXAMPLES 10 AND 11

Example 10

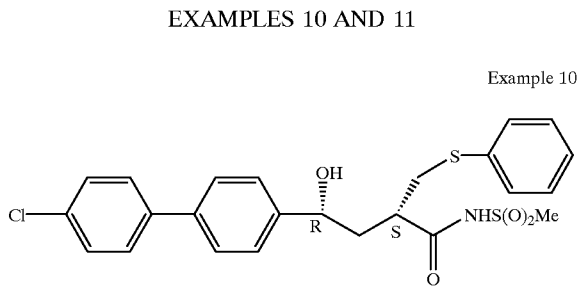

Example 11

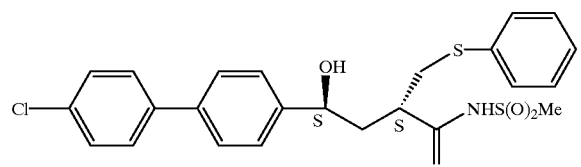

Compound M or N from Example 8 or 9 can be reacted with methanesulfonamide and imidazole or 4-dimethylaminopyridine in dry methylene chloride or tetrahydrofuran at between 0° C. and reflux to yield an intermediate acylsulfonamide which is then deblocked by treatment with tetrabutylammonium fluoride in dry tetrahydrofuran to yield invention compound 10 or 11.

EXAMPLE 12

Example 12

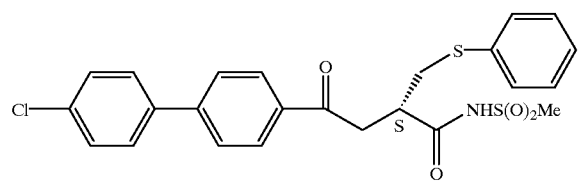

[S]-4-[4-(4-Chlorophenyl)phenyl]-4-oxo-2-(phenylthiomethyl)-butanoic acid is prepared as described in WO-09615096 (Example 197). A dry methylene chloride solution of this ketoacid (1 mmol), methanesulfonamide (1–4 mmol) and 1-hydroxybenzotriazole (1 mmol) can be cooled in an ice bath as 1-ethyl-3-(3-dimethylaminopropyl) carbodiimide methiodide (1–1.5 mmol) is added. After the reaction mixture has stirred for several hours at 0° C., it is left to stir at ambient temperature until a TLC assay indicates that the starting ketoacid has been substantially consumed. The product invention compound can be isolated by dilution with dilute hydrochloric acid, extraction with methylene chloride, evaporation of the extracts and chromatography and/or recrystallization of the residue.

EXAMPLE 13

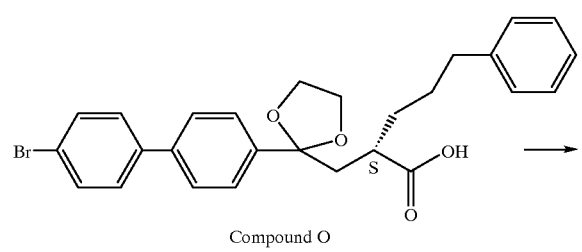

Compound O

-continued

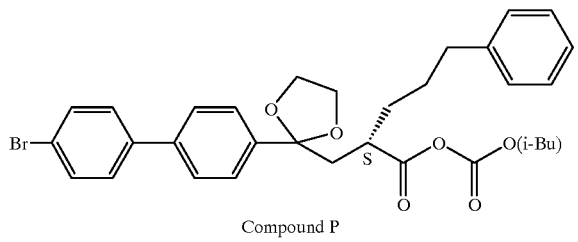

Compound P

Step 1

Compound O is prepared as described in WO-09615096 (Example 178, step 6). Compound O (1 mmol) can be reacted with isobutylchloroformate (1–1.2 mmol) and imidazole (1–2 mmol) in dry methylene chloride or tetrahydrofuran at between −78 and 0° C. to yield the mixed anhydride P which is used directly in solution in the next step.

Example 13

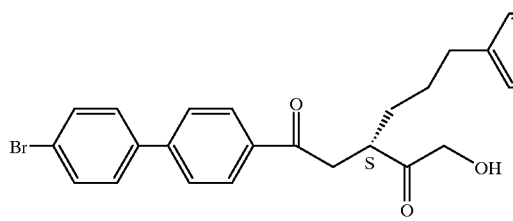

Step 2

Compound P from step 1 (1 mmol) can be reacted with an ether solution of diazomethane with ice bath cooling to yield the diazomethylketone, which is then treated with aqueous sulfuric acid to give the hydroxymethyl ketone invention compound.

EXAMPLE 14

Compound Q

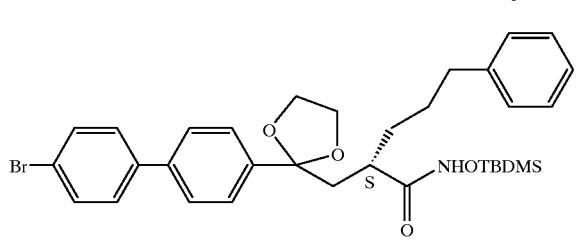

Step 1

Compound P from Example 13 (1 mmol) as a solution in methylene chloride or tetrahydrofuran is stirred at between −78° C. and ambient temperature as O-tert-butyldimethylsilyl hyroxylamine (1–4 mmol) is added. After the reaction mixture has stirred for several hours with cooling, it is left to stir at ambient temperature until a TLC assay indicates that the starting ketoacid has been substantially consumed. The product Q can be isolated by dilution with water, extraction with methylene chloride and evaporation of the extracts in vacuo.

Example 14

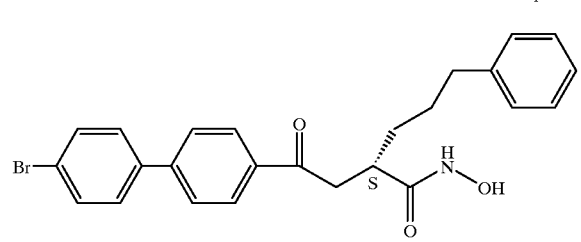

Step 2

Product Q of step 1 (0.1 mmol) can be stirred as a solution in methylene chloride (5 ml) at 0° C. as a drop of concentrated $HClO_4$ is added. After stirring until a TLC assay indicates that the reaction has gone to completion, the invention compound can be isolated by washing the solution to remove the $HClO_4$, evaporation of the solution and chromatography of the residue on silica gel.

EXAMPLE 15

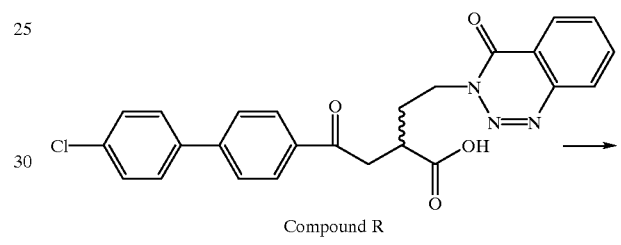

Compound R

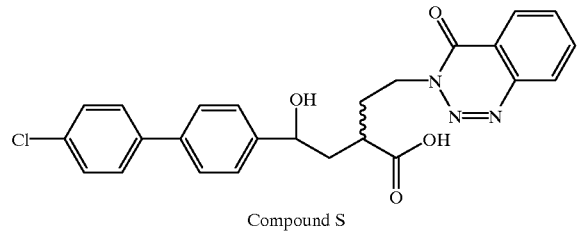

Compound S

Step 1

Compound R above can be prepared according to the procedures described in WO 9743239 (example 19). By using the general procedure of Example 6 (step 1) of this application and Compound R rather than [S]-4-[4-(4-Chlorophenyl)phenyl]-4-oxo-2-(phenylthiomethyl)-butanoic acid, compound S above can be obtained.

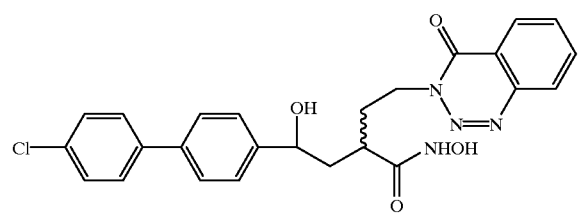

EXAMPLE 15

Steps 2, 3 and 4

By using the general procedures of Example 6 (steps 2, 3 and 4) and Compound S rather than compound F, Example 16 can be obtained.

EXAMPLE 16

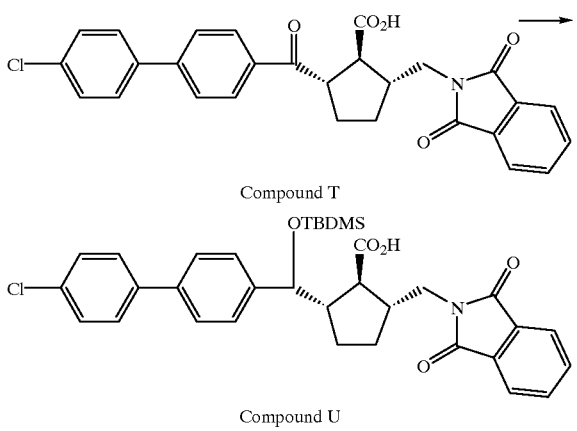

Compound T

Compound U

Step 1

Compound T can be prepared as described in WO 9615096 (Example 361). By using the general procedures of Example 6 of this application (steps 1 and 2) but starting with Compound T rather than [S]-4-[4-(4-Chlorophenyl)phenyl]-4-oxo-2-(phenylthiomethyl)-butanoic acid and using sodium triacetoxyborohydride in tetrahydrofuran rather than sodium borohydride in ethanol, one can obtain Compound U above.

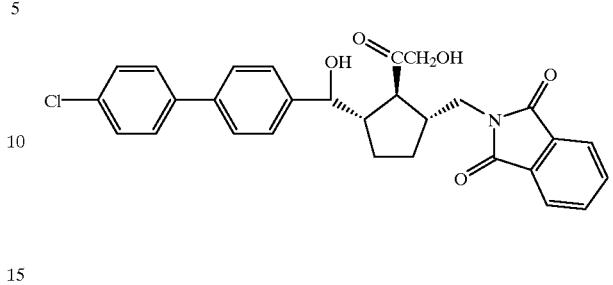

EXAMPLE 16
Steps 2 and 3

By using the general procedures of Example 8 of this application (steps 1 and 2) but starting with Compound U rather than Compound I, one can obtain Example 16.

The Examples in the following tables can be prepared using 4-oxobutanoic acids as starting materials prepared according to the indicated source references together with the general methods of the indicated Example(s) from this application.

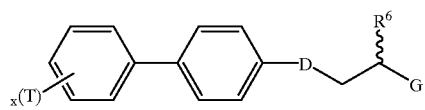

Examples 17–22

| Ex. # | Starting Material Source* | T | D | R⁶ | G | General Method Example(s) |
|---|---|---|---|---|---|---|
| 17 | 1 | 4-OCH₃ | OH (isopropyl) | 4-OH-phenyl—(CH₂)₃— | CH₃C(O)NHOH | 1 |
| 18 | 4 | 4-HOCH₂C≡C— | OH (isopropyl) | phenyl—(CH₂)₃— | CH₃C(O)NHOH | 1 |
| 19 | 5 | 4-PhCH₂O— | OH (isopropyl) | 3-(piperidine-1-carbonyl)phenyl—(CH₂)₂— | CH₃C(O)NHOH | 5 |

-continued

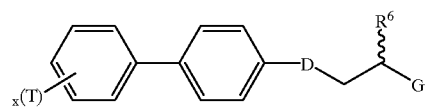

Examples 17–22

| Ex. # | Starting Material Source* | T | D | $R^6$ | G | General Method Example(s) |
|---|---|---|---|---|---|---|
| 20 | 1 | 3-$CH_2CN$ | OH (isopropyl) | phenyl—$(CH_2)_2$— | $CH_2OH$ ketone | 8 |
| 21 | 1 | 4-$OC_5H_{11}$ | OH (isopropyl) | phenyl—$(CH_2)_2$— | $H_3C-SO_2-NH-C(O)-$ | 10 |
| 22 | 1 | 4-Br | =N-OH (oxime) | phenyl-S-ethyl | $H_3C-SO_2-NH-C(O)-$ | 12 then 4 |

*Source 1 is WO 9615096, Source 2 is WO 9743237, Source 3 is WO 9743239, Source 4 is WO 974345, Source 5 is WO 9743247, Source 6 is WO 9809940

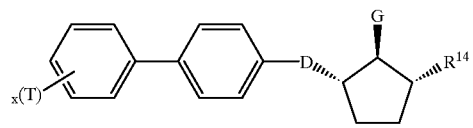

| Ex. # | Starting Material Source* | T | D | $R^{14}$ | G | General Method Example(s) |
|---|---|---|---|---|---|---|
| 23 | 3 | 4-HO-CH₂-C≡C- | OH (isopropyl) | N-ethyl benzisothiazolone dioxide | $-C(O)-NHOH$ | 6 |

| Ex. # | Starting Material Source* | T | D | $R^6$ | G | General Method Example(s) |
|---|---|---|---|---|---|---|

-continued
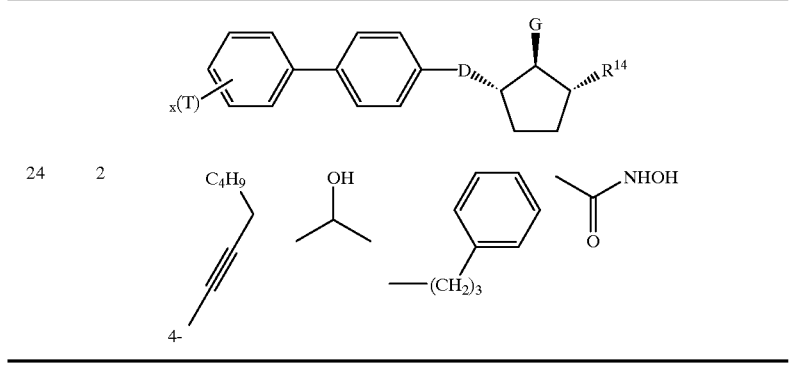
| Ex. # | Starting Material Source* | T | D | R⁶ | G | General Method Example(s) |
|---|---|---|---|---|---|---|
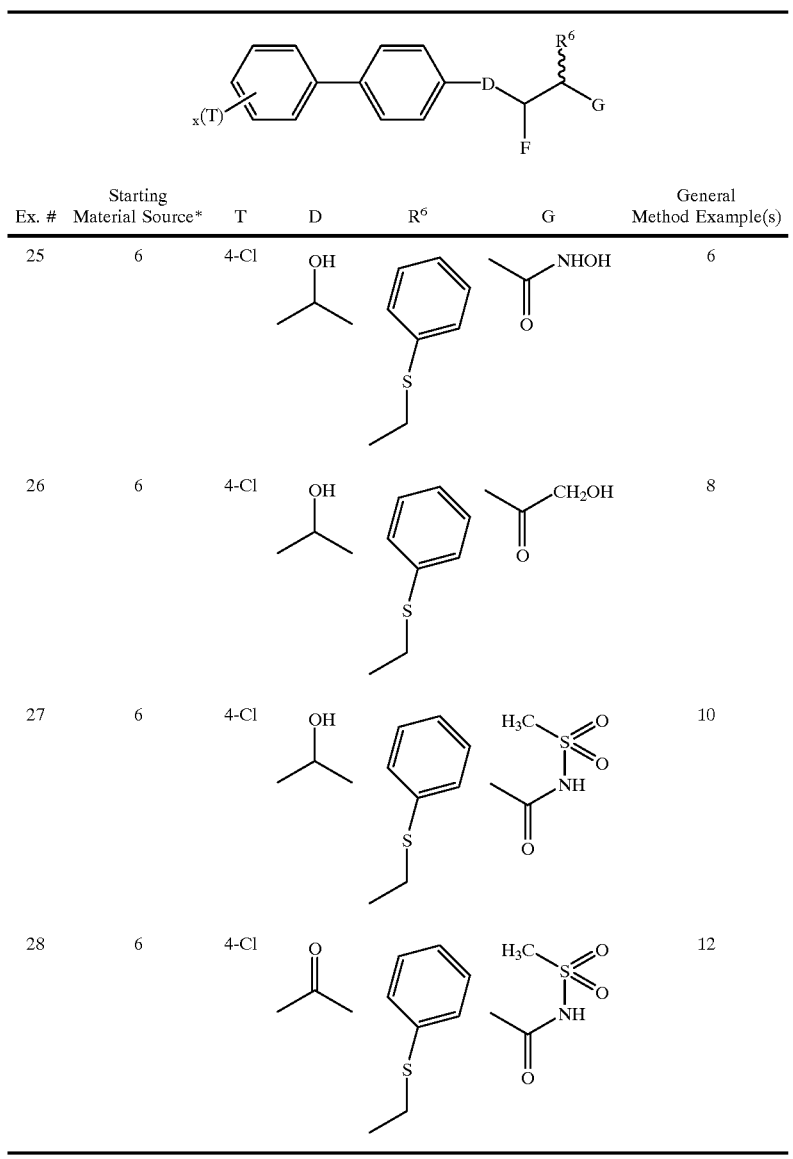
| 24 | 2 | C₄H₉—(at 4-position, alkyne) | OH (isopropyl) | —(CH₂)₃—phenyl | NHOH amide | |
| Ex. # | Starting Material Source* | T | D | R⁶ | G | General Method Example(s) |
|---|---|---|---|---|---|---|
| 25 | 6 | 4-Cl | OH (isopropyl) | phenyl-S-ethyl | C(=O)NHOH | 6 |
| 26 | 6 | 4-Cl | OH (isopropyl) | phenyl-S-ethyl | C(=O)CH₂OH | 8 |
| 27 | 6 | 4-Cl | OH (isopropyl) | phenyl-S-ethyl | H₃C-S(O)₂-NH-C(=O)- | 10 |
| 28 | 6 | 4-Cl | =O (acetone) | phenyl-S-ethyl | H₃C-S(O)₂-NH-C(=O)- | 12 |

Biological Protocols

Inhibitory activities of the compounds of the invention against matrix metalloproteases and production of TNFα may be determined as described below.

Preparation of Gelatinase-B (MMP-9)

MMP-9 is isolated modifying the previously described procedures of Hibbs et al (J. Biol. Chem., 260, 2493–2500, 1984) and Wilhelm et al (J. Biol. Chem., 264, 17213–17221, 1989). Briefly, polymorphonuclear leukocytes (PMN) preparations are isolated as described above from 3 or more units of freshly drawn whole blood. Cells are resuspended in phosphate buffered saline (PBS) containing 100 ng/ml phorbol myristate acetate (PMA) in the presence of 50 mM diisopropylfluorophospate (DFP), 1 μg/ml leupeptin and aprotinin, and 1 mg/ml catalase for 1 hr at 37° C. Supernatants are collected by centrifugation (300×g) and the samples are frozen at −70° C. All chromatographic methods are performed at 4° C. Thawed samples are concentrated 5-fold using an Amicon chamber equipped with a YM-10 membrane. The concentrate is pressure dialyzed against 0.02M Tris-HCl, 0.1 M NaCl, 1 mM $CaCl_2$, 1 μM $ZnCl_2$, 0.001% Brij-35, 0.02% sodium azide ($NaN_3$), pH 7.5 and applied to DEAE ion exchange chromatography resin which is previously equilibrated with the same buffer at a flow rate of 0.4 ml/min. The column is extensively washed with the same buffer and gelatinase is eluted as 4 ml fractions from the column with 0.02M Tris-HCl, 0.5 M NaCl, 1 mM $CaCl_2$, 1 μM $ZnCl_2$, 0.001% Brij-35, 0.02% $NaN_3$, pH 7.5. Gelatinase containing fractions are observed by gelatin zymography (see below), loaded onto a gelatin agarose affinity resin and washed with the same buffer. Gelatinase activity is eluted at a flow rate of 1 ml/min from the column as 1 ml fractions with 0.02M Tris-HCl, 1 M NaCl, 1 mM $CaCl_2$, 1 μM $ZnCl_2$, 0.001% Brij-35, 0.02% $NaN_3$, pH 7.5 containing 10% dimethyl sulfoxide (DMSO). The fractions containing gelatinase activity are pooled and dialyzed against 0.005M Tris-HCl, 5 mM NaCl, 0.5 mM $CaCl_2$, 0.1 μM $ZnCl_2$, 0.001% Brij-35, pH 7.4. The protein content associated with material is determined with a micro-BCA assay (Pierce, Rockford, Ill.), lyophilized and reconstituted to a desired working concentration (100 μg/ml).

Preparation of Gelatinase-A (MMP-2)

Gelatinase A (MMP-2) is prepared using a vaccinia expression system according to the method of R. Fridman, et al., *J. Biol. Chem.*, 267, 15398 (1992).

Preparation of Recombinant Truncated Prostromelysin (MMP-3)

Truncated Prostromelysin-257 is expressed in a soluble form in *E.coli* as described by Marcy et al., Biochemistry, 30, 6476–6483, 1991. Soluble truncated prostromelysin is purified by a modification of the monoclonal antibody affinity chromatography method described by Housley et al., J. Biol. Chem., 268, 4481–87, 1993.

P218 Quenched Fluorescence Assay for MMP-3 Inhibition

This assay was originally described by Knight et al., FEBS Letters, 296, 263–266, 1992, for a related substrate. The assay is run continuously in a 3.0 ml cuvette using a Perkin-Elmer LS 50 B Spectrofluorimeter at 25° C. in a final volume of 2.0 mls. P218 substrate (10 mM) in 100% DMSO is diluted to a final concentration of 2.0 micromolar (μM) into assay buffer: 50 mM MES, pH 6.5 containing 150 mM NaCl, 10 mM CaCl2, 0.005% Brij-35, and 1%(v/v) DMSO. Test compounds(10 mM) in DMSO are diluted in assay buffer at an initial concentration of 10 to 100 micromolar. These are diluted to a final concentration in the assay from 10 nM to 1 μM depending upon their potency previously determined in primary thiopeptilide assay described above.

The reaction is initiated by the addition of recombinant stromelysin (MMP-3) at a final concentration of 1.0 nM. Upon peptide cleavage, the fluorescent MCA group is detected using an excitation wavelength of 328 nanometers and an emission wavelength of 393 nanometers. The assay is linear from 0.2 to 5 nM MMP-3 concentration and percent inhibition is calculated as described above for the primary thiopeptilide assay and $IC_{50}$ values are determined by a linear regression analysis of percent inhibition versus log drug concentration. The peptide sequence of the MCA substrate, hereinafter designated P218, is shown below:

P218

For MMP-3, this substrate has a $K_m$ of 16 μM at pH 6.5 and a $kcat/K_m$ value of $56,000 M^{-1} sec^{-1}$.

Automated MMP Profiling Assay

This assay is run with a protocol analogous to that reported for MMP-3 inhibition using the synthetic peptide P218 and each of the three enzymes and measuring quenched fluorescence. This assay can be run with each invention compound with the three enzymes MMP-3, MMP-9 and MMP-2 in parallel as adapted for a 96-well microtitre plate using a Hamilton AT® workstation.

LPS Induced TNFα Production in Mice

The in vivo inhibitory properties of selected compounds can be determined using a murine LPS induced TNFα production in vivo model. BALB/c mice (Charles River Breeding Laboratories; Kingston, N.Y.) in groups of ten are treated with either vehicle or compound. After one hour, endotoxin (*E. coli* lipopolysaccharide (LPS) 100 mg) is administered intraperitoneally (i.p.). After 90 min, animals are euthanized by carbon dioxide asphyxiation and plasma is obtained from individual animals by cardiac puncture into heparinized tubes. The samples are clarified by centrifugation at 12,500×g for 5 min at 4° C. The supernatants are decanted to new tubes, which are stored as needed at −20° C. TNFα levels in sera are measured using a commercial murine TNF ELISA kit (Genzyme).

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. Compounds having matrix metalloprotease inhibitory activity and the generalized formula:

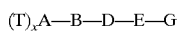

wherein (a) $(T)_xA$ represents substituted or unsubstituted aromatic moiety

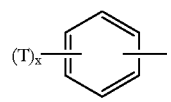

wherein each T represents a substituent group, independently selected from the group consisting of:

the halogens —F, —Cl, —Br, and —I;

alkyl of 1–10 carbons;

haloalkyl of 1–10 carbons;

haloalkoxy of 1–10 carbons;
alkenyl of 2–10 carbons;
alkynyl of 2–10 carbons;
—$(CH_2)_p$Q, wherein
  p is 0 or an integer 1–4,
-alkenyl-Q, wherein
  said alkenyl moiety comprises 2–4 carbons, and
-alkynyl-Q, wherein
  said alkynyl moiety comprises 2–7 carbons; and
  Q is selected from the group consisting of aryl of 6–10 carbons, heteroaryl comprising 4–9 carbons and at least one N, O, S heteroatom, —CN, —CHO, —$NO_2$, —$CO_2R^2$, —$OCOR^2$, —$SOR^3$, —$SO_2R^3$, —$CON(R^4)_2$, —$SO_2N(R^4)_2$, —$C(O)R^2$, —$N(R^4)_2$, —$N(R^2)COR^2$, —$N(R^2)CO_2R^3$, —$N(R^2)CON(R^4)_2$, —$CHN_4$, —$OR^4$, and —$SR^4$;
  wherein
  $R^2$ represents H;
    alkyl of 1–6 carbons;
    aryl of 6–10 carbons;
    heteroaryl comprising 4–9 carbons and at least one N, O, or S heteroatom; or
    arylalkyl in which the aryl portion contains 6–10 carbons and the alkyl portion contains 1–4 carbons; or
    heteroaryl-alkyl in which the heteroaiyl portion comprises 4–9 carbons and at least one N, O, S heteroatom and the alkyl portion contains 1–4 carbons;
  $R^3$ represents alkyl of 1–4 carbons;
    aryl of 6–10 carbons;
    heteroaryl comprising 4–9 carbons and at least one N, O, or S heteroatom; or
    arylalkyl in which the aryl portion contains 6–10 carbons and the alkyl portion contains 1–4 carbons; or
    heteroaryl-alkyl in which the heteroaryl portion comprises 4–9 carbons and at least one N, O, S heteroatom and the alkyl portion contains 1–4 carbons;
  $R^4$ represents H;
    alkyl of 1–12 carbons;
    aryl of 6–10 carbons;
    heteroaryl comprising 4–9 carbons and at least one N, O, or S heteroatom;
    arylalkyl in which the aryl portion contains 6–10 carbons and the alkyl portion contains 1–4 carbons;
    heteroaryl-alkyl in which the heteroaryl portion comprises 4–9 carbons and at least one N, O, S heteroatom and the alkyl portion contains 1–4 carbons;
    alkenyl of 2–12 carbons;
    alkynyl of 2–12 carbons;
    —$(C_qH_{2q}O)_rR^5$ wherein q is 1–3; r is 1–3; and $R^5$ is H provided q is greater than 1, or alkyl of 1–4 carbons, or phenyl;
    alkylenethio terminated with H, alkyl of 1–4 Carbons, or phenyl;
    alkyleneamino terminated with H, alkyl of 1–4 carbons, or phenyl;
    —$(CH_2)_sX$ wherein s is 1–3 and X is halogen;
    —$C(O)OR^2$; or
    —$C(O)R^2$;
    and with the provisos that a) when two $R^4$ groups are situated on a nitrogen, they may be joined by a bond to form a heterocycle, and b) unsaturation in a moiety which is attached to Q or which is part of Q is separated from any N, O, S of Q by at least one carbon atom, and
  x is 0, 1, or 2;
(b) B represents an optionally substituted ring bearing 0–2 substituents T;
(c) D represents $$\diagup_{\diagdown}C=O, \quad \diagup_{\diagdown}C\diagup^H_{OH}, \quad \diagup_{\diagdown}C=NN(R^2)_2, \text{ or } \diagup_{\diagdown}C=NOR^2$$

in which $R^2$ is defined as above and each $R^2$ may be the same or different;
(d) E represents a chain of n carbon atoms bearing m substituents $R^6$, wherein said $R^6$ groups are independent substituents, or constitute spiro or nonspiro rings in which a) two groups $R^6$ are joined, and taken together with the chain atom(s) to which said two R6 group(s) are attached, and any intervening chain atoms, constitute a 3–7 membered ring, or b) one group $R^6$ is joined to the chain on which said one group $R^6$ resides, and taken together with the chain atom(s) to which said R6 group is attached, and any intervening chain atoms, constitutes a 3–7 membered ring; and wherein
  n is 2 or 3;
  m is an integer of 1–3;
  each group $R^6$ is independently selected from the group consisting of:
    fluorine;
    hydroxyl, with the proviso that a single carbon may bear no more than one hydroxyl substituent
    heteroaryl comprising 4–9 carbons and at least one N, O, S heteroatom;
    arylalkyl wherein the aryl portion contains 6–10 carbons and the alkyl portion contains 1–8 carbons;
    heteroaryl-alkyl wherein the heteroaryl portion comprises 4–9 carbons and at least one N, O, S heteroatom, and the alkyl portion contains 1–8 carbons;
    aryl-alkenyl wherein the aryl portion contains 6–10 carbons and the alkenyl portion contains 2–5 carbons;
    heteroaryl-alkenyl wherein the heteroaryl portion comprises 4–9 carbons and at least one N, O, S heteroatom and the alkenyl portion contains 2–5 carbons;
    alkynyl of 2–10 carbons;
    aryl-alkynyl wherein the aryl portion contains 6–10 carbons and the alkynyl portion contains 2–5 carbons;
    heteroaryl-alkynyl wherein the heteroaryl portion comprises 4–9 carbons and at least one N, O, S heteroatom and the alkynyl portion contains 2–5 carbons;
    —$(CH_2)_tR^7$ wherein
      t is 0 or an integer of 1–5; and $R^7$ is selected from the group consisting of

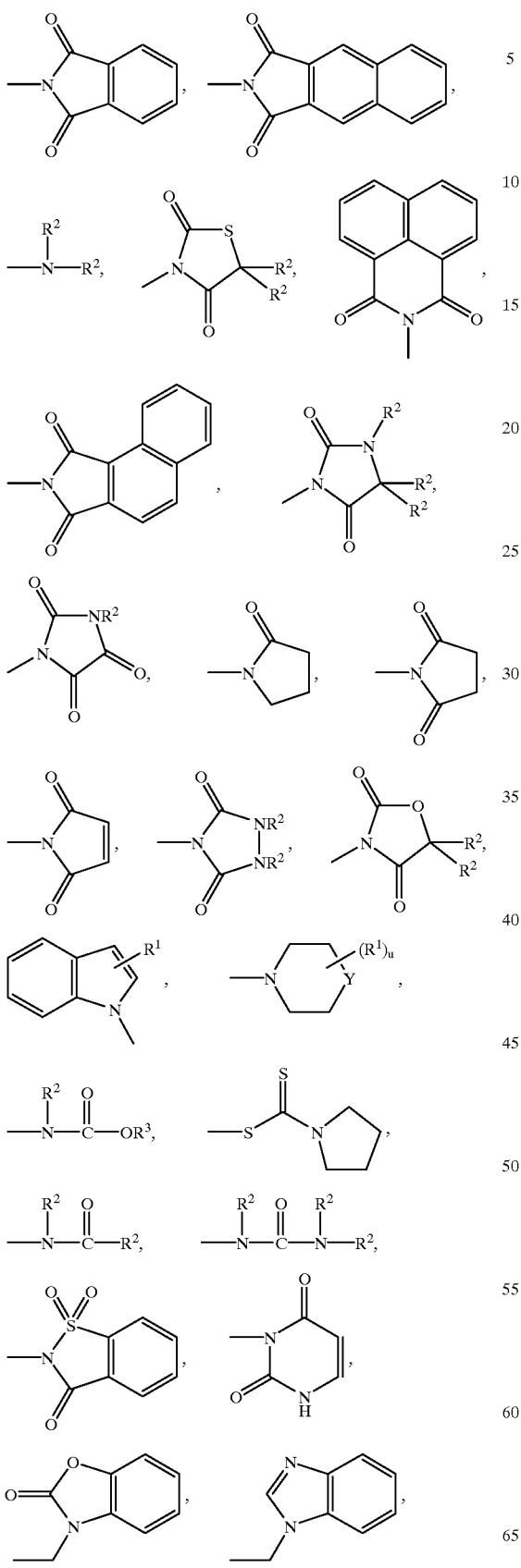

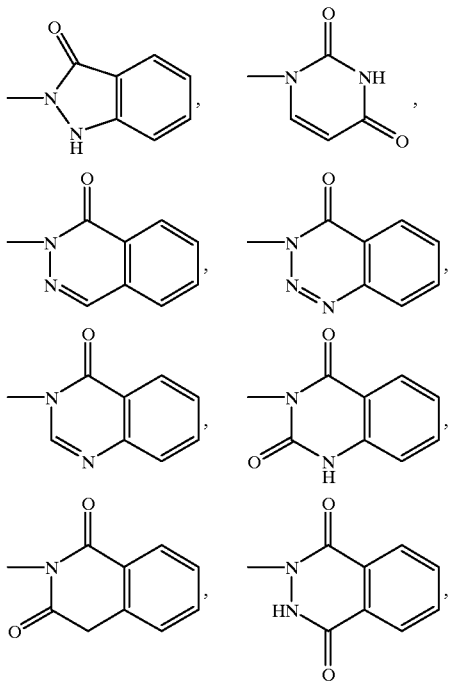

and corresponding heteroaryl moieties in which the aryl portion of an aryl-containing $R^7$ group comprises 4–9 carbons and at least one N, O, S heteroatom;

wherein
   Y represents O or S;
   $R^1$ represents H or alkyl of 1–3 carbons;
   $R^2$ and $R^3$ are as defined above; and
   u is 0, 1, or 2; and
—$(CH_2)_v ZR^8$ wherein
v is 0 or an integer of 1 to 4, with the proviso that when $R^8$ is heteroaryl, v is an integer of 1–4; and
Z represents

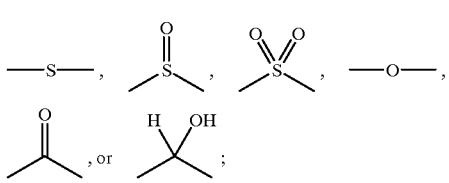

$R^8$ is selected from the group consisting of:
   alkyl of 1 to 12 carbons;
   aryl of 6 to 10 carbons;
   heteroaryl comprising 4–9 carbons and at least one N, O, S heteroatom;
   arylalkyl wherein the aryl portion contains 6 to 12 carbons and the alkyl portion contains 1 to 4 carbons;
   heteroaryl-alkyl wherein the aryl portion comprises 4–9 carbons and at least one N, O, S heteroatom and the alkyl portion contains 1–4 carbons;
   —$C(O)R^9$ wherein $R^9$ represents alkyl of 2–6 carbons, aryl of 6–10 carbons, heteroaryl comprising 4–9 carbons and at least one N, O, S heteroatom, or arylalkyl in which the aryl portion contains 6–10 carbons or is heteroaryl comprising 4–9 carbons and at least one N, O, S heteroatom, and the alkyl portion contains 1–4 carbons;

and with the provisos that when $R^8$ is —C(O)$R^9$, Z is S or O;

when Z is O, $R^8$ may also be —$(C_qH_{2q}O)_rR^5$ wherein q, r, and $R^5$ are as defined above; and —$(CH_2)_wSiR^{10}{}_3$ wherein w is an integer of 1 to 3; and $R^{10}$ represents alkyl of 1 to 2 carbons;

and with the proviso that aryl or heteroaryl portions of any of said T or $R^6$ groups optionally may bear up to two substituents selected from the group consisting of —$(CH_2)_yC(R^4)(R^3)OH$, —$(CH_2)_yOR^4$, —$(CH_2)_ySR^4$, —$(CH_2)_yS(O)R^4$, —$(CH_2)_yS(O)_2R^4$, —$(CH_2)_ySO_2N(R^4)_2$, —$(CH_2)_yN(R^4)_2$, —$(CH_2)_yN(R^4)COR^3$, —$OC(R^4)_2O$— in which both oxygen atoms are connected to the aryl ring, —$(CH_2)_yCOR^4$, —$(CH_2)_yCON(R^4)_2$, —$(CH_2)_yCO_2R^4$, —$(CH_2)_yOCOR^4$, -halogen, —CHO, —$CF_3$, —$NO_2$, —CN, and —$R^3$, wherein y is 0–4; and $R^3$ and $R^4$ are defined as above; and any two $R^4$ which are attached to one nitrogen may be joined to form a heterocycle;

(e) G represents

[chemical structures]

in which $R^3$ is defined as above; and with the proviso that when G is

[chemical structure]

each $R^6$ is an independent substituent;

and pharmaceutically acceptable salts and prodrugs thereof.

2. A compound of claim 1 wherein aryl portions of aryl-containing T and $R^6$ moieties contain only carbon in the rings.

3. A compound of claim 2 wherein the D unit of the general formula of claim 1 is a —CHOH— group.

4. A compound of claim 2 wherein in the E unit of the general formula of claim 1, n is 2 and m is 1.

5. A compound of claim 2 wherein the G unit of the general formula of claim 1 is —C(O)NHOH.

6. A compound of claim 2 wherein m is 1; and $R^6$ is an independent substituent.

7. A compound of claim 6 having the formula

[chemical structure]

wherein x is 1 or 2; and one substituent T is located on the 4-position of said A ring, relative to the point of attachment between said A and B rings.

8. A compound of claim 2 wherein m is 2 or 3; and when m is 2, both groups $R^6$ are independent substituents, or together constitute a spiro ring, or one group $R^6$ is an independent substituent and the other constitutes a spiro ring; and when m is 3, two groups $R^6$ are independent substituents and one group $R^6$ constitutes a ring, or two groups R6 constitute a ring and one group R6 is an independent substituent, or three groups R6 are independent substituents.

9. A compound of claim 2 wherein m is 1 or 2; and when m is 1, the group $R^6$ constitutes a nonspiro ring;

when m is 2, both groups $R^6$ together constitute a nonspiro ring or one group R6 is an independent substituent and the other constitutes a nonspiro ring.

10. A compound of claim 9 wherein said E unit is selected from the group consisting of

[chemical structures]

wherein a is 0, 1, or 2; b is 0 or 1; c is 0 or 1; d is 0 or 1; c+d is 0 or 1; e is 1–5; g is 3–5; i is 0–4; k is 0–2; the total number of groups $R^6$ is 0, 1, or 2; U represents O, S, or $NR^1$; and each group $R^{14}$ is independently selected from the group consisting of:

alkyl of 1–9 carbons;

arylalkyl wherein the alkyl portion contains 1–7 carbons and the aryl portion contains 6–10 carbons;

alkenyl of 2–9 carbons;
aryl-substituted alkenyl wherein the alkenyl portion contains 2–4 carbons and the aryl portion contains 6–10 carbons;
alkynyl of 2–9 carbons;
aryl-substituted alkynyl wherein the alkynyl portion contains 2–4 carbons and the aryl portion contains 6–10 carbons;
aryl of 6–10 carbons;
—COR$^2$;
—CH(OH)R$^2$
—CO$_2$R$^3$;
—CON(R$^2$)$_2$;
—(CH$_2$)$_t$R$^7$ wherein
t is 0 or an integer of 1–4; and
—(CH$_2$)$_v$ZR$^8$ wherein
v is 0 or an integer of 1 to 3; and
Z represents —S—, —S(O)—, —S(O)$_2$ or —O—.

11. A compound of claim 10 having the formula

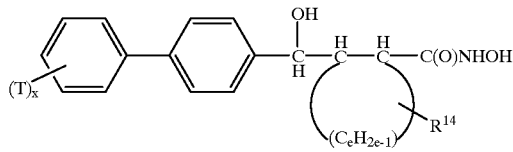

wherein
the subscript x is 1 or 2;
one substituent T is located on the 4-position of said A ring, relative to the point of attachment between said A and B rings; and
e is 2 or 3.

12. A composition having matrix metalloprotease inhibitory activity, comprising a compound of claim 1 and a pharmaceutically acceptable carrier.

13. A method of treating a mammal to achieve an effect, wherein the effect is: alleviation of osteoarthritis; alleviation of rheumatoid arthritis; alleviation of septic arthritis; alleviation of autoimmune disease; alleviation of autoimmune encephalomyelitis; alleviation of periodontal disease; alleviation of corneal ulceration; alleviation of proteinuria; alleviation of aneurysmal aortic disease; alleviation of dystrophobic epidermolysis bullosa; alleviation of diseases of abnormal bone loss; alleviation of tempero mandibular joint disease; alleviation of demyelinating diseases of the nervous system; alleviation of chronic obstructive pulmonary disease; alleviation of acute and chronic neurodegenerative disorders; alleviation of cardiovascular and pulmonary diseases; alleviation of decubital ulcers; alleviation of aneurysmal diseases; alleviation of metabolic diseases; alleviation of cachexia; alleviation of premature skin aging; alleviation of diseases linked to TNFα production; retardation of tumor metastasis; retardation of tumor frowth or angiogenesis associated with tumor growth; retardation of degenerative cartilage loss following traumatic joint injury; reduction of pain; reduction of coronary thrombosis from atherosclerotic plaque rupture; improved birth control or improved wound repair; the method comprising administering an amount of a compound of claim 1 which is effective to inhibit the activity of at least one matrix metalloprotease or inhibit the production of TNFα, or both, in said mammal, thereby to achieve said effect.

* * * * *